US006048660A

United States Patent [19]
Leppard et al.

[11] Patent Number: 6,048,660
[45] Date of Patent: Apr. 11, 2000

[54] NON-VOLATILE PHENYLGLYOXALIC ESTERS

[75] Inventors: David George Leppard, Marly, Switzerland; Manfred Köhler, Freiburg, Germany

[73] Assignee: Ciba Specialty Chemicals Corporation, Tarrytown, N.Y.

[21] Appl. No.: 09/014,555

[22] Filed: Jan. 28, 1998

[30] Foreign Application Priority Data

Jan. 30, 1997 [CH] Switzerland ................ 195/97

[51] Int. Cl.[7] .............. G03C 1/492; C08F 2/46; C07D 307/93; C07C 321/100
[52] U.S. Cl. ............ 430/270.1; 430/325; 430/281.1; 522/8; 522/37; 549/465; 560/9; 560/53
[58] Field of Search ............ 560/51, 53, 9; 522/37, 8; 549/465; 430/270.1, 281.1, 325

[56] References Cited

U.S. PATENT DOCUMENTS

| | | | |
|---|---|---|---|
| 3,532,737 | 10/1970 | Siggins | 260/476 |
| 3,657,325 | 4/1972 | Siggins | 260/483 |

(List continued on next page.)

FOREIGN PATENT DOCUMENTS

| | | |
|---|---|---|
| 0132868 | 2/1985 | European Pat. Off. . |
| 1534320 | 11/1978 | United Kingdom . |

OTHER PUBLICATIONS

Hu, S. et al Tetrahedron, 53, 6, 2751–2766, 1997.

(List continued on next page.)

*Primary Examiner*—Janet Baxter
*Assistant Examiner*—Rosemary Ashton
*Attorney, Agent, or Firm*—Kevin T. Mansfield; Luther A.R. Hall

[57] ABSTRACT

Compounds of the formula I $$R_1-\underset{O}{\underset{\|}{C}}-\underset{O}{\underset{\|}{C}}-O-Y-O-\underset{O}{\underset{\|}{C}}-\underset{O}{\underset{\|}{C}}-R_2, \quad (I)$$

in which
$R_1$ and $R_2$ independently of one another are, for example, a group of the formula II (II) [substituted benzene ring with $R_3$, $R_4$, $R_5$, $R_6$, $R_7$]

$R_3$, $R_4$, $R_5$, $R_6$ and $R_7$ independently of one another are, for example, hydrogen, $C_1$–$C_{12}$alkyl, $OR_8$, $SR_9$, $NR_{10}R_{11}$, halogen or phenyl; $R_8$, $R_9$, $R_{10}$, $R_{11}$ independently of one another are, for example, hydrogen or $C_1$–$C_{12}$alkyl; $R_{12}$ is, for example, $C_1$–$C_8$alkyl; $R_{13}$ is, for example, $C_1$–$C_{12}$alkyl; $R_{14}$ is, for example, hydrogen; Y is $C_1$–$C_{12}$alkylene, $C_4$–$C_8$alkenylene, $C_4$–$C_8$alkynylene or cyclohexylene, or is phenylene or $C_4$–$C_{40}$alkylene interrupted one or more times by —O—, —S— or —$NR_{15}$—, or Y is a group of the formula III, IV, V, VI, VII, VIII, IX, X or XI (III) [bis-phenyl-C(CH$_3$)$_2$ group]

(IV) [bis-cyclohexyl-C(CH$_3$)$_2$ group]

(V) —$CH_2CH(OH)CH_2O$—$Y_1$—$OCH_2CH(OH)CH_2$—

(VI) —$CH_2CH(OH)CH_2$—

(VII) [bicyclic furan structure]

(VIII) —$CH_2$—$\underset{\underset{CH_2OH}{|}}{\overset{\overset{CH_2OH}{|}}{C}}$—$CH_2$—

(IX) —$CH_2$—$\underset{\underset{CH_2O-\underset{O}{\underset{\|}{C}}-\underset{O}{\underset{\|}{C}}-R_1}{|}}{\overset{\overset{R_{16}}{|}}{C}}$—$CH_2$—

(X)

$$-CH_2-\underset{\underset{CH_2O-\underset{O}{\underset{\|}{C}}-\underset{O}{\underset{\|}{C}}-R_1}{|}}{\overset{\overset{CH_2O-\underset{O}{\underset{\|}{C}}-\underset{O}{\underset{\|}{C}}-R_1}{|}}{C}}-CH_2-$$

(XI)

—$CH_2$—[phenylene]—$CH_2$—

$Y_1$ is as defined for Y with the exception of the formula V; $R_{15}$ is hydrogen, $C_1$–$C_{12}$alkyl or phenyl; and $R_{16}$ is hydrogen, $CH_2OH$ or $C_1$–$C_4$alkyl; and mixtures of these compounds with further photoinitiators are suitable for photopolymerizing compounds having ethylenically unsaturated double bonds.

15 Claims, No Drawings

U.S. PATENT DOCUMENTS

| | | | |
|---|---|---|---|
| 3,704,313 | 11/1972 | Diamond | 260/520 |
| 3,754,006 | 8/1973 | Siggins | 260/332.2 A |
| 3,930,868 | 1/1976 | Muzyczko et al. | 96/115 P |
| 4,038,164 | 7/1977 | Via | 204/159.15 |
| 4,279,718 | 7/1981 | Schuster et al. | 204/159.15 |
| 4,308,394 | 12/1981 | Shuster et al. | 560/51 |
| 4,475,999 | 10/1984 | Via | 204/159.23 |
| 4,507,187 | 3/1985 | Jacolune et al. | 204/159.13 |
| 4,987,159 | 1/1991 | Bassi et al. | 522/36 |
| 5,795,581 | 8/1998 | Segalman et al. | 424/400 |

OTHER PUBLICATIONS

Angewandte Makromolekulare Chemie 93 (1981), pp. 83–95.

Hu et al., Tetrahedron, vol. 53, No. 8, pp. 2751–2766, Feb. 24, 1997.

NON-VOLATILE PHENYLGLYOXALIC ESTERS

This application relates to non-volatile phenylglyoxalic esters, to their use as photoinitiators, alone and in mixtures with other initiators, and to photocurable compositions comprising the compounds of the invention.

Simple phenylglyoxalic esters, in some cases in combination with sensitizer compounds, have already been described as photoinitiators in, for example, U.S. Pat. Nos. 4,475,999 and 4,038,164, EP-A 132 868 and GB-A 1 534 320.

U.S. Pat. No. 4,507,187 discloses phenylglyoxalates comprising siloxane groups as photoinitiators. U.S. Pat. Nos. 4,279,718, 4,308,394 and 3,930,868 discloses arylglyoxylates with acrylic acid radicals as photoinitiators for incorporation by polymerization into certain binders. In *Angew. Makromol. Chemie* 93 (1981), 83–95 W. Mayer, H. Rudolph and E. de Cleur describe, inter alia, ammonium salts of phenylglyoxalic acid as latent photoinitiators.

In industry there is a need for reactive photoinitiators of low volatility. It has now been found that certain phenylglyoxalic esters are particularly suitable as photoinitiators of low volatility. These are compounds of the formula 1, in which two phenylglyoxalic ester radicals are connected via a bridging group Y.

The invention therefore provides compounds of the formula I

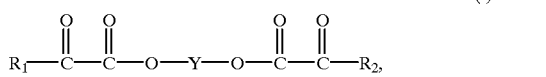

(I)

in which $R_1$ and $R_2$ independently of one another are a group of the formula II

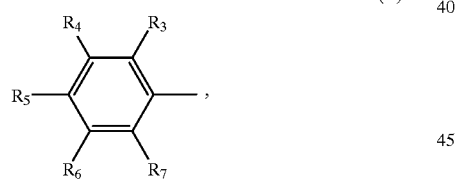

(II)

or naphthyl, anthracyl, phenanthryl or a heterocyclic radical, the radicals naphthyl, anthracyl, phenanthryl and heterocycle being unsubstituted or substituted by $C_1-C_8$alkyl, phenyl, $OR_8$, $SR_9$ and/or $NR_{10}R_{11}$, and where the substituents $OR_8$, $SR_9$, $NR_{10}R_{11}$ can form 5- or 6-membered rings by way of the radicals $R_8$, $R_9$, $R_{10}$ and/or $R_{11}$ with further substituents on the naphthyl, anthracyl or phenanthryl ring or heterocycle or with one of the C atoms of the naphthyl, anthracyl or phenanthryl ring or heterocycle;

$R_3$, $R_4$, $R_5$, $R_6$ and $R_7$ independently of one another are hydrogen or are $C_1-C_{12}$alkyl which is unsubstituted or substituted by OH, $C_1-C_4$alkoxy, phenyl, naphthyl, halogen, CN and/or —$OCOR_{12}$, or are $C_2-C_{12}$alkyl which is interrupted by one or more O atoms, or $R_3$, $R_4$, $R_5$, $R_6$ and $R_7$ are $OR_8$, $SR_9$, $NR_{10}R_{11}$, halogen or phenyl which is unsubstituted or substituted by one or two $C_1-C_4$alkyl and/or one or two $C_1-C_4$alkoxy substituents, where the substituents $OR_8$, $SR_9$, $NR_{10}R_{11}$ can form 5- or 6-membered rings by way of the radicals $R_8$, $R_9$, $R_{10}$ and/or $R_{11}$ with further substituents on the phenyl ring or with one of the C atoms of the phenyl ring;

$R_8$ and $R_9$ independently of one another are hydrogen or are $C_1-C_{12}$alkyl which is unsubstituted or substituted by OH, $C_1-C_4$alkoxy, phenyl, phenoxy and/or $OCOR_{12}$, or are $C_2-C_{12}$alkyl which is interrupted by one or more O atoms, or $R_8$ and $R_9$ are unsubstituted or $C_1-C_4$alkoxy-, phenyl- and/or $C_1-C_4$alkyl-substituted phenyl, $C_3-C_6$alkenyl, cyclopentyl, cyclohexyl or naphthyl;

$R_{10}$ and $R_{11}$ independently of one another are hydrogen or are $C_1-C_{12}$alkyl which is unsubstituted or substituted by OH, $C_1-C_4$alkoxy and/or phenyl, or are $C_2-C_{12}$alkyl which is interrupted by one or more O atoms, or $R_{10}$ and $R_{11}$ are phenyl, —$COR_{12}$ or $SO_2R_{13}$, or $R_{10}$ and $R_{11}$, together with the nitrogen atom to which they are attached, form a 5-, 6- or 7-membered ring which may additionally be interrupted by —O— or —$NR_{14}$—;

$R_{12}$ is $C_1-C_8$alkyl or is phenyl which is unsubstituted or substituted by one to three $C_1-C_4$alkyl and/or one to three $C_1-C_4$alkoxy substituents;

$R_{13}$ is $C_1-C_{12}$alkyl, phenyl or 4-methylphenyl;

$R_{14}$ is hydrogen or is $C_1-C_8$alkyl which is unsubstituted or substituted by OH or $C_1-C_4$alkoxy or is phenyl which is unsubstituted or substituted by OH, $C_1-C_4$alkyl or $C_1-C_4$alkoxy;

Y is $C_1-C_{12}$alkylene, $C_4-C_8$-alkenylene, $C_4-C_8$alkynylene, cyclohexylene, $C_4-C_{40}$alkylene interrupted one or more times by —O—, —S— or —$NR_{15}$—, or is phenylene, or Y is a group of the formula III, IV, V, VI, VII, VIII, IX, X or XI

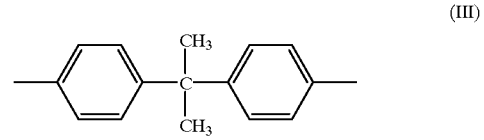

(III)

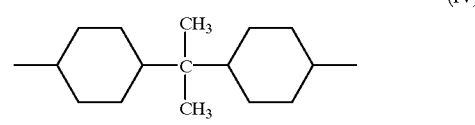

(IV)

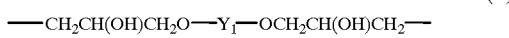

(V)

(VI)

(VII)

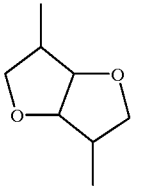

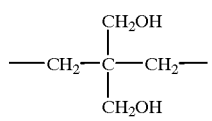
(VIII)

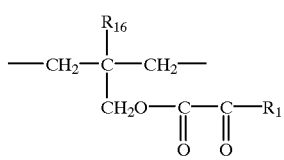
(IX)

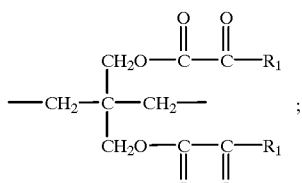
(X)

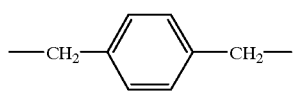
(XI)

$Y_1$ is as defined for Y with the exception of the formula V;

$R_{15}$ is hydrogen, $C_1$–$C_{12}$alkyl or phenyl; and $R_{16}$ is hydrogen, $CH_2OH$ or $C_1$–$C_4$alkyl.

$C_1$–$C_{12}$alkyl is linear or branched and is, for example, $C_1$–$C_8$-, $C_1$–$C_6$- or $C_1$–$C_4$alkyl. Examples are methyl, ethyl, propyl, isopropyl, n-butyl, sec-butyl, iso-butyl, tert-butyl, pentyl, hexyl, heptyl, 2,4,4-trimethylpentyl, 2-ethylhexyl, octyl, nonyl, decyl, undecyl or dodecyl. For example, $R_3$, $R_4$, $R_5$, $R_6$, $R_7$, $R_8$, $R_9$, $R_{10}$, $R_{11}$, $R_{13}$ and $R_{15}$ are $C_1$–$C_8$alkyl, especially $C_1$–$C_6$alkyl, preferably $C_1$–$C_4$alkyl, such as methyl or butyl, for example.

$C_1$–$C_8$alkyl and $C_1$–$C_4$alkyl are likewise linear or branched and have, for example, the meanings indicated above up to the corresponding number of C atoms. $R_{12}$ and $R_{14}$ are, for example $C_1$–$C_6$-, especially $C_1$–$C_4$alkyl, preferably methyl or butyl.

$C_1$–$C_4$alkyl is preferably methyl.

$R_{16}$ as $C_1$–$C_4$alkyl is preferably ethyl or methyl.

$C_2$–$C_{12}$alkyl which is interrupted one or more times by —O— is, for example, interrupted 1–9 times, for example 1–7 times or once or twice by —O—. This results, for example, in-structural units such as —$CH_2$—O—$CH_3$, —$CH_2CH_2$—O—$CH_2CH_3$, —[$CH_2CH_2O$]$_y$—$CH_3$, where y=1–5, —($CH_2CH_2O$)$_5CH_2CH_3$, —$CH_2$—$CH(CH_3)$—O—$CH_2$—$CH_2CH_3$ or —$CH_2$—$CH(CH_3)$—O—$CH_2$—$CH_3$.

$C_1$–$C_4$alkoxy stands for linear or branched radicals and is, for example, methoxy, ethoxy, propoxy, isopropoxy, n-butyloxy, sec-butyloxy, iso-butyloxy or tert-butyloxy, especially methoxy, n-butyloxy or tert-butyloxy, preferably methoxy.

Y as $C_1$–$C_{12}$alkylene is linear or branched alkylene, for example $C_1$–$C_8$-, $C_1$–$C_6$- or $C_1$–$C_4$alkylene, such as methylene, ethylene, propylene, isopropylene, n-butylene, sec-butylene, isobutylene, tert-butylene, pentylene, hexylene, heptylene, octylene, nonylene, decylene or dodecylene. In particular Y is, for example, ethylene, decylene,

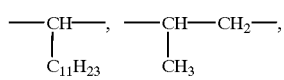

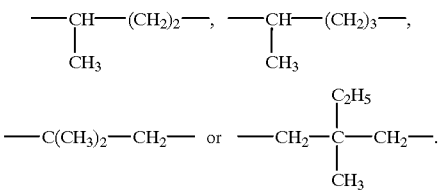

Y is preferably $C_2$–$C_8$alkylene, especially $C_2$–$C_6$alkylene.

Y as $C_4$–$C_{40}$alkylene interrupted by —O—, —S— or —$NR_{15}$— results, for example, in structural units such as —$CH_2CH_2$—O—$CH_2CH_2$—, —[$CH_2CH_2O$]$_y$—, where y=2–20, —($CH_2CH_2O$)$_{18}CH_2CH_2$—, —$CH_2$—$CH(CH_3)$—O—$CH_2$—$CH(CH_3)$—, —$CH_2CH_2$—S—$CH_2CH_2$—, —$CH_2CH_2CH_2$—S—$CH_2CH_2CH_2$—, —($CH_2$)$_3$—S—($CH_2$)$_3$—S—($CH_2$)$_3$—, —$CH_2CH_2$—($NR_{15}$)—$CH_2CH_2$—. Y is, for example, $C_4$–$C_{18}$- or $C_4$–$C_{12}$alkylene interrupted by —O—, —S— or —$NR_{15}$—.

Y is preferably $C_4$–$C_{40}$alkylene interrupted by —O—, for example —$CH_2CH_2$—O—$CH_2CH_2$— and —[$CH_2CH_2O$]$_y$—, where y=2–10, especially y=2–5.

$C_4$–$C_8$alkenylene radicals can be mono- or polyunsaturated and are, for example, 2-methyl-2-propenylene, 1-butenylene, 2-butenylene, 1,3-pentadienylene, 1-hexenylene or 1-octenylene, especially 1-butenylene and 2-butenylene.

$C_4$–$C_8$alkynylene radicals can be mono- or polyunsaturated. Examples are, in particular, 1-butynylene or 2-butynylene.

Cyclohexylene is 1,4-, 1,2- or 1,3-cyclohexylene, especially 1,4-cyclohexylene.

Phenylene is 1,4-, 1,2- or 1,3-phenylene, especially 1,4-phenylene.

Heterocyclic radical refers in this context to both aliphatic rings and aromatic 5- or 6-membered rings containing one or two heteroatoms. Examples of suitable heteroatoms in this context are O, N or S. Examples are furyl, thienyl, pyrrolyl, oxinyl, dioxinyl or pyridyl. Heteroaryl stands for aromatic 5- or 6-membered rings containing one or two heteroatoms.

Where naphthyl, anthracyl, phenanthryl or heteroaryl rings substituted by $OR_8$, $SR_9$ or $NR_{10}R_{11}$ form 5- or 6-membered rings with the radicals $R_8$, $R_9$, $R_{10}$ and/or $R_{11}$, then examples of the rings thereby embraced are the following structures:

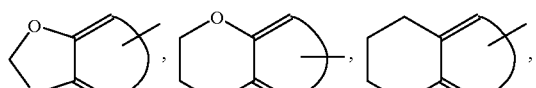

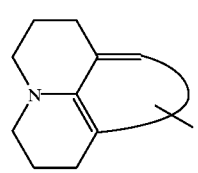

where the arc and the two double bonds represent the respective aromatic ring system.

Where $R_3$, $R_4$, $R_5$, $R_6$ or $R_7$ as $OR_8$, $SR_9$ or $NR_{10}R_{11}$ form a 5- or 6-membered ring with one C atom of the phenyl ring, then examples of the structures thereby embraced are the following systems

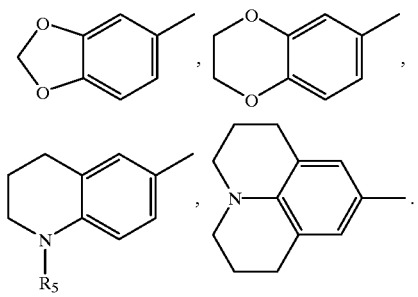

Phenyl substituted once or twice by $C_1$–$C_4$alkyl and/or once or twice by $C_1$–$C_4$alkoxy, and phenyl substituted once to three times by $C_1$–$C_4$alkyl and/or once to three times by $C_1$–$C_4$-alkoxy, is substituted, for example, in positions 2,6, 2,4, 2,3, 2,5 or 2,4,6 of the phenyl ring. Examples are 2,6-dimethylphenyl, 2,4-dimethylphenyl, 2,5-dimethylphenyl, 2,6-dimethoxyphenyl, 2,4-dimethoxyphenyl, 2,5-dimethoxyphenyl, 2,6-dimethoxy-4-methylphenyl or 2,4,6-trimethylphenyl, 2,4,6-trimethoxyphenyl.

Halogen is fluorine, chlorine, bromine or iodine, especially chlorine or bromine, preferably chlorine.

If $C_1$–$C_{12}$alkyl is substituted one or more times by halogen then there are, for example, 1 to 3 or 1 or 2 halogen substituents on the alkyl radical.

If $R_{10}$ and $R_{11}$, together with the N atom to which they are attached, form a 5- or 6-membered ring which may additionally be interrupted by —O— or —$NR_{14}$—, then examples of the rings concerned are morpholine, pyrrole, pyrrolidine, imidazolidine, piperidine or piperazine rings, preferably morpholine, piperidine or piperazine rings, in particular a morpholine ring.

Preference is given to compounds of the formula I in which $R_1$ and $R_2$ are a radical of the formula II.

Further compounds of the formula I that are of interest are those in which $R_1$ and $R_2$ are identical.

Compounds of the formula I worthy of emphasis are those in which Y is $C_2$–$C_8$alkylene, $C_4$alkenylene, $C_4$alkynylene, cyclohexylene, or is $C_4$–$C_{18}$alkylene interrupted one or more times by —O—, or Y is a group of the formula V, VI, IX, X or XI.

Y is preferably $C_2$–$C_6$alkylene, $C_4$–$C_{12}$alkylene interrupted one or more times by —O—, or a group of the formula IX.

Particular preference is given to those compounds of the formula I in which $R_3$, $R_4$, $R_5$, $R_6$ and $R_7$ independently of one another are hydrogen, $C_1$–$C_4$alkyl, chlorine, $OR_8$, $SR_9$ or $NR_{10}R_{11}$ and where the substituent $OR_8$ can form 5- or 6-membered rings by way of the radical $R_8$ with further substituents on the phenyl ring or with one of the C atoms of the phenyl ring.

Compounds of the formula I that are of interest are those in which $R_1$ and R2 are a radical of the formula II, $R_4$ and $R_5$ independently of one another are hydrogen, $OR_8$ or $SR_9$, $R_3$, $R_6$ and $R_7$ are hydrogen, $R_8$ and $R_9$ are $C_1$–$C_4$alkyl and Y is linear or branched $C_2$–$C_6$alkylene, phenylene or a group of the formula XI or is $C_4$–$C_6$alkylene interrupted once or twice by —O— or —S—.

Preference is given, furthermore, to the compounds of the formula I in which $R_3$, $R_4$, $R_5$, $R_6$ and $R_7$ independently of one another are hydrogen, chlorine, phenyl, unsubstituted or OH—, $C_1$–$C_4$alkoxy- or phenyl-subsituted $C_1$–$C_{12}$alkyl, or $C_2$–$C_{12}$alkyl interrupted by —O—, or $R_3$, $R_4$, $R_5$, $R_6$ and $R_7$ are $OR_8$, $SR_9$, $NR_{10}R_{11}$, where the subsituents $OR_8$, $SR_9$, $NR_{10}R_{11}$ can form 5- or 6-membered rings by way of the radicals $R_8$, $R_9$, $R_{10}$ and/or $R_{11}$, with further substituents on the phenyl ring or with one of the C atoms of the phenyl ring.

Likewise preferred are compounds of the formula I in which $R_8$ is hydrogen or unsubstituted or OH—, $C_1$–$C_4$alkoxy-, phenyl- or phenoxy-substituted $C_1$–$C_{12}$alkyl or $R_8$ is $C_1$–$C_{12}$-alkyl interrupted by —O—, phenyl, allyl or cyclohexyl.

In particular, $R_8$ is hydrogen, unsubstituted or $C_1$–$C_4$alkoxy-substituted $C_1$–$C_4$alkyl or phenyl.

Also worthy of emphasis are compounds of the formula I in which $R_9$ is unsubstituted or OH— or $C_1$–$C_4$alkoxy-substituted $C_1$–$C_{12}$alkyl or $R_9$ is $C_2$–$C_{12}$alkyl which is interrupted by —O— or $R_9$ is unsubstituted $C_1$–$C_4$alkyl-and/or $C_1$–$C_4$alkoxy-substituted phenyl.

In particular, $R_9$ is unsubstituted or $C_1$–$C_4$alkoxy-substituted $C_1$–$C_4$alkyl or phenyl.

Further preferred compounds of the formula I are those in which $R_{10}$ and $R_{11}$ are identical and are $C_1$–$C_4$alkyl or in which $R_{10}$ and $R_{11}$, together with the N atom to which they are attached, form a 6-membered ring which may be interrupted by O.

$R_{14}$ is preferably hydrogen or $C_1$–$C_4$alkyl.

I. The compounds of the formula I of the invention can be prepared, for example, by reacting diols (A) with arylglyoxalic monoesters (B), such as the corresponding methyl ester, for example, in the presence of a catalyst:

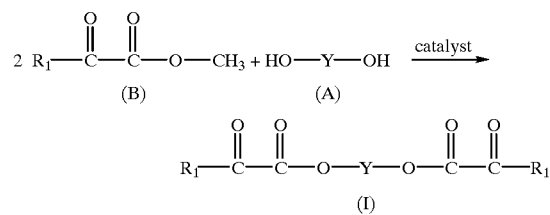

$R_1$ is as defined above.

The catalyst used is one of the catalysts familiar to the skilled worker for transesterification reactions, such as dibutyltin oxide or p-toluenesulfonic acid, for example.

II. A further possibility to obtain the compounds of the invention is the base-catalysed reaction of arylglyoxalic halides (C), preferably the chlorides, with a diol (A):

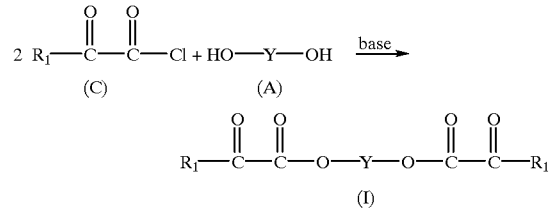

The bases to be used for such reactions are familiar to the skilled worker. Aqueous bases should not be employed. Examples of suitable bases are carbonates, tertiary amine bases, such as triethylamine, or pyridine, for example.

III. It is also possible to obtain the compounds of the invention, for example, by reacting diols (A) with corresponding arylacetic esters (D) in the presence of a catalyst and with subsequent oxidation:

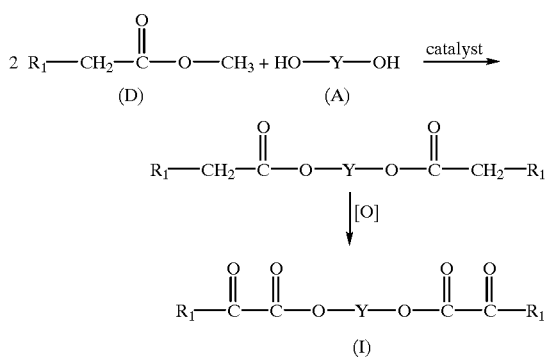

Examples of catalysts which can be employed are those described under I. The oxidation step can take place, for example, as described in *J. Chem. Soc. Chem. Comm.* (1993), 323 or in *Synthesis* (1994), 915.

IV. A further suitable preparation method for the compounds of the formula I of the invention is, for example, the reaction of corresponding hydroxy-substituted arylacetic esters (E) with diols (A) and with subsequent oxidation:

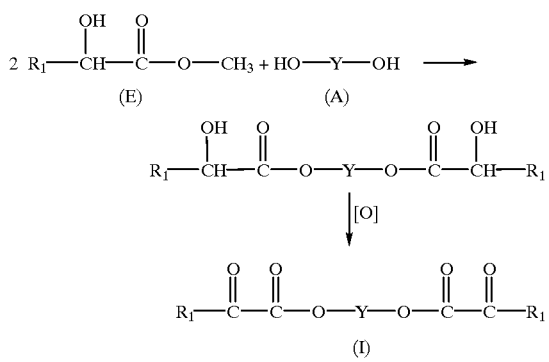

The oxidation can be carried out, for example, by the method described in *J. Chem. Soc. Chem. Comm.* (1994), 1807.

V. A further preparation option for the compounds of the formula I of the invention is the acid-catalysed reaction of arylcarboxylic cyanides (F) with diols (A):

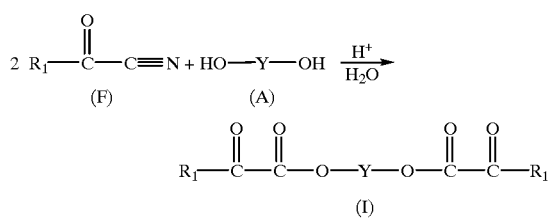

VI. The compounds of the formula I of the invention can also be obtained, for example, by Friedel-Crafts reaction of aryls with dimeric oxocarboxylic chlorides (H) in the presence of aluminium chloride:

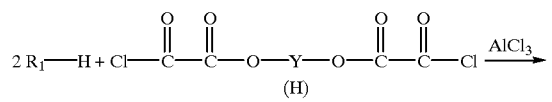

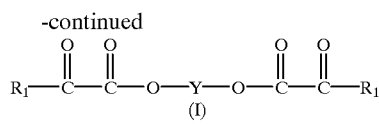

Catalysts which can be used are the catalysts which are familiar to the skilled worker and are customary for Friedel-Crafts reactions, examples being tin chloride, zinc chloride, aluminium chloride, titanium chloride or acid earths.

In the preparation of asymmetric compounds of the formula I, i.e. those in which $R_1$ and $R_2$ have different definitions, the reaction is carried out using the appropriate, differing precursors, judiciously in a ratio of 1:1.

In general, the reactions I, III and IV can be carried out without using a solvent, with one of the reaction components which is liquid, for example the diol, acting as solvent. It is also possible, however, to carry out the reactions in an inert solvent. Examples of suitable solvents are aliphatic or aromatic hydrocarbons such as alkanes and alkane mixtures, cyclohexane, benzene, toluene or xylene, for example. The boiling point of these solvents, however, should lie above that of the alcohol which is formed in the course of the reaction.

The other syntheses set out above are judiciously conducted in an inert solvent. Suitable examples are those indicated above.

In the case of reactions I, III and IV it is judicious to ensure that the alcohol which forms in the course of the reaction is removed from the reaction mixture. This takes place, for example, by distillation.

The reactions are carried out at different temperatures depending on the starting materials and solvents used. The temperatures and other reaction conditions required for the corresponding reactions are generally known and are familiar to the skilled worker.

The reaction products can be separated and purified by general, customary methods, for example by crystallization, distillation or chromatography.

The preparation of the starting materials required to synthesize the compounds of the formula I of the invention is generally known and is familiar to the skilled worker. The starting materials (B), (C), (D) and (F) where $R_1$=phenyl, indeed, are obtainable commercially.

For instance, the arylglyoxalic esters (B), for example, are obtained by Friedel-Crafts reaction from the aryls and from the correpsonding oxocarboxylic methyl ester chloride, or by esterifying arylglyoxalic chlorides (C) with alcohols.

Arylglyoxalic chlorides (C) can be obtained, for example, by chlorinating the corresponding acid with, for example, $SOCl_2$.

Arylcarboxylic cyanides (F) can be obtained, for example, by reacting the corresponding acid chlorides with CuCN.

The preparation of arylacetic methyl esters (D) is possible, for example, by acid-catalysed reaction of aryl-$CH_2$—CN with methanol. This reaction is described, for example, in *Org. Syn. Coll. Vol. I,* 270. The corresponding aryl-$CH_2$-cyanides can be obtained, for example, from the corresponding chlorides using NaCN, as is disclosed, for example, in *Org. Syn. Coll.* Vol. I, 107 and *Org. Syn. Coll.* Vol IV, 576.

The synthesis of arylacetic ethyl esters (D) is to be found, for example, in *J. Chem. Soc. Chem. Comm* (1969), 515, the corresponding aryl bromide being reacted with $N_2CH_2COOC_2H_5$ in the presence of Li/diethyl ether, CuBr. Another method, the reaction of aryl bromides with ethyl acetate and NaH, is described, for example, in *J. Am. Chem.*

Soc. (1959) 81, 1627. *J. Org. Chem.* (1968) 33, 1675 sets out the Grignard reaction of aryl bromides with $BrCH_2COOC_2H_5$ to give the arylacetic ethyl ester (D).

The preparation of the diols (A) is familiar to the skilled worker and is widely described in the literature. Many of these compounds are obtainable commercially.

In accordance with the invention the compounds of the formula I can be used as photoinitiators for the photopolymerization of ethylenically unsaturated compounds or of mixtures which include such compounds. This use can also be practised in combination with another photoinitiator and/or other additives.

The invention therefore additionally provides photopolymerizable compositions comprising (a) at least one ethylenically unsaturated photopolymerizable compound and (b) as photoinitiator, at least one compound of the formula I, it also being possible for the composition, in addition to component (b), to comprise other photoinitiators (c) and/or other additives (d).

The unsaturated compounds may include one or more olefinic double bonds. They may be of low (monomeric) or high (oligomeric) molecular mass. Examples of monomers containing a double bond are alkyl or hydroxyalkyl acrylates or methacrylates, for example methyl, ethyl, butyl, 2-ethylhexyl or 2-hydroxyethyl acrylate, isobornyl acrylate, methyl methacrylate or ethyl methacrylate. Silicone acrylates are also advantageous. Other examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride.

Examples of monomers containing two or more double bonds are the diacrylates of ethylene glycol, propylene glycol, neopentyl glycol, hexamethylene glycol or of bisphenol A, and 4,4'-bis(2-acryl-oyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl) isocyanurate.

Examples of polyunsaturated compounds of relatively high molecular mass (oligomers) are acrylisized epoxy resins, acrylisized polyesters, polyesters containing vinyl ether or epoxy groups, and also polyurethanes and polyethers. Further examples of unsaturated oligomers are unsaturated polyester resins, which are usually prepared from maleic acid, phthalic acid and one or more diols and have molecular weights of from about 500 to 3000. In addition it is also possible to employ vinyl ether monomers and oligomers, and also maleate-terminated oligomers with polyester, polyurethane, polyether, polyvinyl ether and epoxy main chains. Of particular suitability are combinations of oligomers which carry vinyl ether groups and of polymers as described in WO 90/01512. However, copolymers of vinyl ether and maleic acid-functionalized monomers are also suitable. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, for example unsaturated polyesters, polyamides and polyurethanes and copolymers thereof, alkyd resins, polybutadiene and butadiene copolymers, polyisoprene and isoprene copolymers, polymers and copolymers containing (meth)acrylic groups in side chains, and also mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxydiphenyl, 2,2-di(4-hydroxyphenyl)propane, and also novolaks and resols. Examples of polyepoxides are those based on the above-mentioned polyols, especially the aromatic polyols, and epichlorohydrin. Other suitable polyols are polymers and copolymers containing hydroxyl groups in the polymer chain or in side groups, examples being polyvinyl alcohol and copolymers thereof or polyhydroxyalkyl methacrylates or copolymers thereof. Further polyols which are suitable are oligoesters having hydroxyl end groups.

Examples of aliphatic and cycloaliphatic polyols are alkylenediols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glcyol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or completely esterified with one carboxylic acid or with different unsaturated carboxylic acids, and in partial esters the free hydroxyl groups may be modified, for example etherified or esterified with other carboxylic acids.

Examples of esters are:

trimethylolpropane triacrylate, trimethylolethane triacrylate, trimethylolpropane trimeth-acrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol tris-itaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetra methacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol with a molecular weight of from 200 to 1500, or mixtures thereof.

Also suitable as components (a) are the amides of identical or different, unsaturated carboxylic acids with aromatic, cycloaliphatic and aliphatic polyamines having preferably 2 to 6, especially 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β- aminoethoxy)- or di(β-aminopropoxy)ethane. Other suitable polyamines are polymers and copolymers, preferably with additional amino groups in the side chain, and oligoamides having amino end groups. Examples of such unsaturated amides are methylenebisacrylamide, 1,6-hexamethylenebisacrylamide, diethylenetriaminetrismethacrylamide, bis(methacrylamidopropoxy)ethane, β-methacrylamidoethyl methacrylate and N[(β-hydroxyethoxy)ethyl]acrylamide.

Suitable unsaturated polyesters and polyamides are derived, for example, from maleic acid and from diols or diamines. Some of the maleic acid can be replaced by other dicarboxylic acids. They can be used together with ethylenically unsaturated comonomers, for example styrene. The polyesters and polyamides may also be derived from dicarboxylic acids and from ethylenically unsaturated diols or diamines, especially from those with relatively long chains of, for example 6 to 20 C atoms. Examples of polyurethanes are those composed of saturated or unsaturated diisocyanates and of unsaturated or, respectively, saturated diols.

Polybutadiene and polyisoprene and copolymers thereof are known. Examples of suitable comonomers are olefins, such as ethylene, propene, butene and hexene, (meth) acrylates, acrylonitrile, styrene or vinyl chloride. Polymers with (meth)acrylate groups in the side chain are likewise known. They may, for example, be reaction products of epoxy resins based on novolaks with (meth)acrylic acid, or may be homo- or copolymers of vinyl alcohol or hydroxyalkyl derivatives thereof which are esterified with (meth) acrylic acid, or may be homo- and copolymers of (meth) acrylates which are esterified with hydroxyalkyl (meth) acrylates.

The photopolymerizable compounds can be used alone or in any desired mixtures. It is preferred to use mixtures of polyol (meth)acrylates.

Binders as well can be added to these novel compositions, and this is particularly expedient when the photopolymerizable compounds are liquid or viscous substances. The quantity of binder may, for example, be 5–95%, preferably 10–90% and especially 40–90%, by weight relative to the overall solids content. The choice of binder is made depending on the field of application and on properties required for this field, such as the capacity for development in aqueous and organic solvent systems, adhesion to substrates and sensitivity to oxygen.

Examples of suitable binders are polymers having a molecular weight of about 5000 to 2000000, preferably 10000 to 1000000. Examples are: homo- and copolymers of acrylates and methacrylates, for example copolymers of methyl methacrylate/ethyl acrylate/methacrylic acid, poly (alkyl methacrylates), poly(alkyl acrylates); cellulose esters and cellulose ethers, such as cellulose acetate, cellulose acetobutyrate, methylcellulose, ethylcellulose; polyvinylbutyral, polyvinylformal, cyclized rubber, polyethers such as polyethylene oxide, polypropylene oxide and polytetrahydrofuran; polystyrene, polycarbonate, polyurethane, chlorinated polyolefins, polyvinyl chloride, vinyl chloride/vinylidene copolymers, copolymers of vinylidene chloride with acrylonitrile, methyl methacrylate and vinyl acetate, polyvinyl acetate, copoly(ethylene/vinyl acetate), polymers such as polycaprolactam and poly (hexamethylenadipamide), and polyesters such as poly (ethylene glycol terephtalate) and poly(hexamethylene glycol succinate) and polyimides.

The unsaturated compounds can also be used as a mixture with non-photopolymerizable, film-forming components. These may, for example, be physically drying polymers or solutions thereof in organic solvents, for instance nitrocellulose or cellulose acetobutyrate. They may also, however, be chemically and/or thermally curable (heat-curable) resins, examples being polyisocyanates, polyepoxides and melamine resins, as well as polyimide precursors. The use of heat-curable resins at the same time is important for use in systems known as hybrid systems, which in a first stage are photopolymerized and in a second stage are crosslinked by means of thermal aftertreatment.

The photoinitiators according to the invention are further suitable as initiators for curing of oxidative drying systems, such as are for example described in "Lehrbuch der Lacke und Beschichtungen", Vol. III, 296–328, Verlag W. A. Colomb in Heenemann GmbH, Berlin-Ober-schwandorf (1976).

In addition to the photoinitiator the photopolymerizable mixtures may include various additives (d). Examples of these are thermal inhibitors, which are intended to prevent premature polymerization, examples being hydroquinone, hydroquinine derivatives, p-methoxyphenol, β-naphthol or sterically hindered phenols, such as 2,6-di-tert-butyl-p-cresol. In order to increase the stability on storage in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. To exclude atmospheric oxygen during the polymerization it is possible to add paraffin or similar wax-like substances which, being of inadequate solubility in the polymer, migrate to the surface in the beginning of polymerization and form a transparent surface layer which prevents the ingress of air. It is also possible to apply an oxygen-impermeable layer. Light stabilizers which can be added in a small quantity are UV absorbers, for example those of the hydroxyphenylbenzotriazole, hydroxyphenylbenzophenone, oxalamide or hydroxyphenyl-s-triazine type. These compounds can be used individually or in mixtures, with or without sterically hindered amines (HALS).

Examples of such UV absorbers and light stabilizers are 1. 2-(2'-hydroxyphenyl)benzotriazoles for example 2-(2'-hydroxy-5'-methylphenyl)benzo-triazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotrizole, 2-(2'-hydroxy-4'-octoxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)-benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethyl-hexyl-oxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)-benzotriazole, 2-(3'-tert-butyl-2'-hydroxy-5'-(2-octyloxycarbonylethyl)phenyl) benzotriazole, 2-(3'-tert-butyl-5'-[2-(2-ethylhexybxy) carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonyl-ethyl)phenylbenzotriazole, 2,2'-methylenebis[4-(1,1,3,3-tetramethylbutyl)-6-benzotriazol-2-yl-phenol]; transesterification product of 2-[3'-tert-butyl-5'-(2-methoxycarbonylethyl)-2'-hydroxy-phenyl]-benzotriazole with polyethylene glycol 300; [R—CH$_2$CH$_2$—COO(CH$_2$)$_3$]$_2$— where R=3'-tert-butyl-4'-hydroxy-5'-2H-benzotriazol-2-yl-phenyl.

2. 2-Hydroxybenzophenones, for example the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy derivative.

3. Esters of substituted or unsubstituted benzoicacids, for example 4-tert-butylphenyl salicylate, phenyl salicylate, octylphenyl salicylate, dibenzoylresorcinol, bis(4-tert-butylbenzoy)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, and 2-methyl-4,6-di-tert-butylphenyl 3,5-di-tert-butyl-4-hydroxybenzoate.

4. Acrylates, for example isooctyl or ethyl α-cyano-β,β-diphenyl acrylate, methyl α-carbomethoxycinnamate, butyl or methyl α-cyano-β,β-methyl-p-methoxycinnamate, methyl α-carboxymethoxy-p-methoxycinnamate and N-(β-carbomethoxy-β-cyanovinyl)-2-methylindoline.

5. Sterically hindered amines, for example bis-(2,2,6,6-tetramethylpiperidyl) sebacate, bis-(2,2,6,6-tetramethylpiperidyl) succinate, bis-(1,2,2,6,6-pentamethylpiperidyl) sebacate, bis-(1,2,2,6,6-pentamethylpiperidyl) n-butyl-3,5-di-tert-butyl-4-hydroxybenzylmalonate, condensation product of 1-hydroxyethyl-2,2,6,6-tetramethyl-4-hydroxypiperidine and succinic acid, condensation product of N,N'-bis-(2,2,6,6-tetramethyl-4-piperidyl)hexa-methylenediamine and 4-tert-octylamino-2,6-dichloro-1,3,5-s-triazine, tris-(2,2,6,6-tetramethyl-4-piperidyl) nitrilotriacetate, tetrakis-(2,2,6,6-tetramethyl-4-piperidyl)-1,2,3,4-butane tetraoate, 1,1'-(1,2-ethandiyl)bis(3,3,5,5-tetramethyl-piperazinone), 4-benzoyl-2,2,6,6-tetramethylpiperidine, 4-stearyloxy-2,2,6,6-tetramethylpiperidine, bis-(1,2,2,6,6-pentamethylpiperidyl) 2-n-butyl-2-(2-hydroxy-3,5-di-tert-butylbenzyl) malonate, 3-n-octyl-7,7,9,9-tetramethyl-1,3,8-triazaspiro-[4.5]decane-2,4-dione, bis-(1-octyloxy-2,2,6,6-tetramethylpiperidyl) sebacate, bis-(1-octyloxy-2,2,6,6-tetramethylpiperidyl) succinate, condensation product of N,N'-bis-(2,2,6,6-tetramethyl-4-piperidyl) hexamethylenediamine and 4-morpholino-2,6-dichloro-1,3,5-triazine, condensation product of 2-chloro-4,6-di-(4-n-butylamino-2,2,6,6-tetramethylpiperidyl)-1,3,5-triazine and 1,2-bis-(3-aminopropyl-amino)ethane, condensation product of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidine-2,5-dione and 3-dodecyl-1-(1,2,2,6,6-pentamethyl-4-piperidyl)-pyrrolidine-2,5-dione.

6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'di-tert-butyloxanilide, 2-ethoxy-2'-ethyl-oxanilide, N,N'-bis-(3-dimethylaminopropyl)oxalamide, 2-ethoxy-5-tert-butyl-2'-ethyloxanilide and its mixture with 2-ethoxy-2'-ethyl-5,4'-di-tert-butyloxanilide, mixtures of o- and p-methoxy- and of o- and p-ethoxy-disubstituted oxanalides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis-(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxy-phenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxy-propyloxy)phenyl]-4,6-bis(2,4-dimethylphenyl)-1,3,5-triazine, 2-[2-hydroxy-4-(2-hydroxy-3-octyloxy-propyloxy)phenyl]-4,6-bis(2,4-dimethylphenyl)-1,3,5-triazine, 2-[4-dodecyl/tridecyl-oxy-(2-hydroxypropyl)oxy-2-hydroxy-phenyl]-4,6-bis(2,4-dimethylphenyl)-1,3,5-triazine.

8. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythrityl diphosphite, tris-(2,4-di-tert-butylphenyl) phosphite, diisodecyl pentaerythrityl diphosphite, bis-(2,4-di-tert-butylphenyl) pentaerythrityl diphosphite, bis-(2,6-di-tert-butyl-4-methylphenyl) pentaerythrityl diphosphite, bisisodecyloxy pentaerythrityl diphosphite, bis-(2,4-di-tert-butyl-6-methylphenyl) pentaerythrityl diphosphite, bis-(2,4,6-tri-tert-butylphenyl) pentaerythrityl diphosphite, tristearyl sorbityl triphosphite, tetrakis-(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyl-dibenzo[d,g]-1,3,2-dioxaphosphocine, bis-(2,4-di-tert-butyl-6-methylphenyl) methyl phosphite and bis(2,4-di-tert-butyl-6-methylphenyl) ethyl phosphite.

Further additives known in the art may be added, as for example flow improvers and adhesion promoters.

To accelerate the photopolymerization it is possible to add amines, for example triethanolamine, N-methyldiethanolamine, p-dimethylaminobenzoate or Michler's ketone. The action of the amines can be intensified by the addition of aromatic ketones of the benzophenone type. Examples of amines which can be used as oxygen scavengers are substituted N,N-dialkylanilines, as are described in EP-A 339841. Other accelerators, coinitiators and autoxidizers are thiols, thioethers, disulfides, phosphonium salts, phosphine oxides or phosphines, as described, for example, in EP-A 438123, in GB-A 2180358 and in JP-A Hei 6-68309.

It is further possible to add chain transfer agents which are customary in the art to the compositions according to the invention. Examples are mercaptanes, amines and benzothiazol.

Photopolymerization can also be accelerated by adding further photosensitizers as further additive (d) which shift or broaden the spectral sensitivity. These are, in particular, aromatic carbonyl compounds, for example benzophenone, thioxanthone, anthraquinone and 3-acylcoumarin derivatives, and also 3-(aroylmethylene)thiazolines, camphor quinone, but also eosine, rhodamine and erythrosine dyes. Also the above described amines may be considered as photosensitizers.

The curing process can be assisted by, in particular, compositions which are pigmented (for example with titanium dioxide), and also by adding a component which under thermal conditions forms free radicals, for example an azo compound such as 2,2'-azobis(4-methoxy-2,4-dimethylvaleronitrile), a triazene, diazo sulfide, pentazadiene or a peroxy compound, for instance a hydroperoxide or peroxycarbonate, for example t-butyl hydroperoxide, as described for example in EP-A 245639.

The compositions according to the invention may comprise as further additive (d) a photoreducable dye, e.g., xanthene-, benzoxanthene-, benzothioxanthene, thiazine-, pyronine-, porphyrine- or acridine dyes, and/or trihalogenmethyl compounds which can be cleaved by irradiation. Similar compositions are for example described in EP-A 445624.

Further customary additives (d), depending on the intended use, are optical brighteners, fillers, pigments, dyes, wetting agents or levelling assistants. In order to cure thick and pigmented coatings it is appropriate to add glass microspheres or pulverized glass fibres, as described for example in U.S. Pat. No. 5,013,768.

The choice of additive is made depending on the field of application and on properties required for this field. The additives (d) described above are customary in the art and accordingly are added in amounts which are usual in the respective application.

The invention also provides compositions comprising as component (a) at least one ethylenically unsaturated photopolymerizable compound which is emulsified or dissolved in water. Many variants of such radiation-curable aqueous prepolymer dispersions are commercially available. A prepolymer dispersion is understood as being a dispersion of water and at least one prepolymer dispersed therein. The concentration of water in these systems is, for example, from 5 to 80% by weight, in particular from 30 to 60% by weight. The concentration of the radiation-curable prepolymer or prepolymer mixture is, for example, from 95 to 20% by weight, in particular from 70 to 40% by weight. In these compositions the sum of the percentages given for water and prepolymer is in each case 100, with auxiliaries and additives being added in varying quantities depending on the intended use.

The radiation-curable, film-forming prepolymers which are dispersed in water and are often also dissolved are aqueous prepolymer dispersions of mono- or polyfunctional, ethylenically unsaturated prepolymers which are known per se, can be initiated by free radicals and have for example a content of from 0.01 to 1.0 mol of polymerizable double bonds per 100 g of prepolymer and an average molecular weight of, for example, at least 400, in particular from 500 to 10 000. Prepolymers with higher molecular weights, however, may also be considered depending on the intended application. Use is made, for example, of polyesters containing polymerizable C—C double bonds and having an acid number of not more than 10, of polyethers containing polymerizable C—C double bonds, of hydroxyl-containing reaction products of a polyepoxide, containing at least two epoxide groups per molecule, with at least one α,β-ethylenically unsaturated carboxylic acid, of polyurethane (meth)acrylates and of acrylic copolymers which contain α,β3-ethylenically unsaturated acrylic radicals, as are described in EP-A 12339. Mixtures of these prepolymers can likewise be used. Also suitable are the polymerizable prepolymers described in EP-A 33896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions, based on specific alkyl (meth)acrylate polymers, are described in EP-A 41125, and suitable water-dispersible, radiation-curable prepolymers of urethane acrylates can be found in DE-A 2936039.

Further additives which may be included in these radiation-curable aqueous prepolymer dispersions are dispersion auxiliaries, emulsifiers, antioxidants, light stabilizers, dyes, pigments, fillers, for example talc, gypsum, silicic acid, rutile, carbon black, zinc oxide, iron oxides, reaction accelerators, levelling agents, lubricants, wetting agents, thickeners, flatting agents, antifoams and other auxiliaries customary in paint technology. Suitable dispersion auxiliaries are water-soluble organic compounds which are of high molecular mass and contain polar groups, examples being polyvinyl alcohols, polyvinylpyrrolidone or cellulose ethers. Emulsifiers which can be used are nonionic emulsifiers and, if desired, ionic emulsifiers as well.

In certain cases it may be of advantage to use mixtures of two or more of the novel photoinitiator systems. It is of course also possible to use mixtures with known photoinitiators, for example mixtures with benzophenone, benzophenone derivatives, acetophenone, acetophenone derivatives, for example α-hydroxycycloalkyl phenyl ketones or 2-hydroxy- 2-methyl-1-phenyl-propanone, dialkoxyacetophenones, α-hydroxy- or α-aminoacetophenones, e.g. (4-methylthiobenzoyl)-1-methyl-1-morpholinoethane, (4-morpholinobenzoyl)-1-benzyl-1-dimethylaminopropane, 4-aroyl-1,3-dioxolanes, benzoin alkyl ethers and benzil ketals, e.g. dimethyl benzil ketal, phenyiglyoxalic esters and derivatives thereof, monoacyl phosphine oxides, e.g. (2,4,6-trimethylbenzoyl) diphenylphosphine oxide, bisacyiphosphine oxides, e.g. bis (2,6-dimethoxy-benzoyl)-(2,4,4-trimethyl-pentyl)phosphine oxide, bis(2,4,6-trimethylbenzoyl)-phenylphosphine oxide, bis(2,4,6-trimethylbenzoyl)-2,4-dipentoxyphenylphosphine oxide, trisacyiphosphine oxides, ferrocenium compounds, or titanocenes, e.g. bis(cyclopentadienyl)-bis(2,6-difluoro-3-pyrryl-phenyl)titanium.

Where the novel photoinitiator systems are employed in hybrid systems, use is made, in addition to the novel free-radical hardeners, of cationic photoinitiators, for example peroxide compounds such as benzoyl peroxide (other suitable peroxides are described in U.S. Pat. No. 4,950,581 column 19, lines 17–25), aromatic sulfonium-, phosphonium- or iodonium salts as described for example in U.S. Pat. No. 4,950,581, column 18, line 60 to column 19, line 10 or cyclopentadienyl-arene-iron(II) complex salts, for example ($\eta^6$-iso-propylbenzene) ($\eta^5$-cyclopentadienyl)iron (II) hexafluorophosphate.

The invention also provides compositions in which the additional photoinitiators (c) are compounds of the formula XII, XIII, XIV, XV or mixtures thereof,

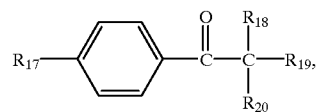
(XII)

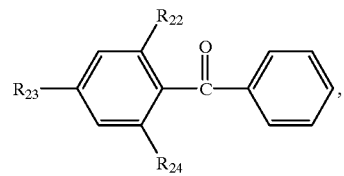
(XIII)

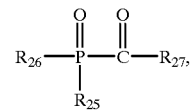
(XIV)

-continued

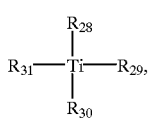
(XV)

in which

R$_{17}$ is hydrogen, C$_1$–C$_8$alkyl, C$_1$–C$_{18}$alkoxy, —OCH$_2$CH$_2$—OR$_{21}$, morpholino, SCH$_3$, a group

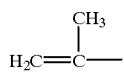

or a group

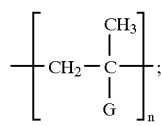

n has a value from 2 to 10;

G is the radical

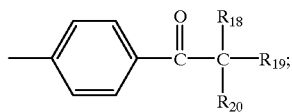

R$_{18}$ is hydroxyl, C$_1$–C$_{16}$alkoxy, morpholino, dimethylamino or —O(CH$_2$CH$_2$O)$_m$—C$_1$–C$_{16}$alkyl;

R$_{19}$ and R$_{20}$ independently of one another are hydrogen, C$_1$–C$_6$alkyl, phenyl, benzyl, C$_1$–C$_{16}$alkoxy or —O(CH$_2$CH$_2$O)$_m$—C$_1$–C$_{16}$alkyl, or R$_{19}$ and R$_{20}$, together with the carbon atom to which they are attached, form a cyclohexyl ring;

m is a number 1–20;

where R$_{18}$, R$_{19}$ and R$_{20}$ are not all simultaneously C$_1$–C$_{16}$alkoxy or —O(CH$_2$CH$_2$O)$_m$—C$_1$–C$_{16}$alkyl, and R$_{21}$ is hydrogen,

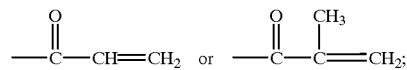

R$_{22}$ and R$_{24}$ independently of one another are hydrogen or methyl;

R$_{23}$ is hydrogen, methyl or phenylthio, where the phenyl ring of the phenylthio radical can be substituted in positions 4, 2, 2,4 or 2,4,6 by C$_1$–C$_4$alkyl;

R$_{25}$ and R$_{26}$ independently of one another are C$_1$–C$_{20}$alkyl, cyclohexyl, cyclopentyl, phenyl, naphthyl or biphenylyl, where the radicals cyclohexyl, cyclopentyl, phenyl, naphthyl or biphenylyl are unsubstituted or subsituted by halogen, C$_1$–C$_{12}$alkyl and/or C$_1$–C$_{12}$alkoxy, or R$_{25}$ is an S- or N-containing 5- or 6-membered heterocyclic ring, or are

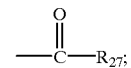

R$_{27}$ is cyclohexyl, cyclopentyl, phenyl, naphthyl or biphenylyl, where the radicals cyclohexyl, cyclopentyl, phenyl, naphthyl or biphenylyl are unsubstituted or substituted by halogen, C$_1$–C$_4$alkyl and/or C$_1$–C$_4$alkoxy, or R$_{27}$ is an S- or N-containing 5- or 6-membered heterocyclic ring;

R$_{28}$ and R$_{29}$ independently of one another are cyclopentadienyl which is unsubstituted or substituted once, twice or three times by C$_1$–C$_{18}$alkyl, C$_1$–C$_{18}$alkoxy, cyclopentyl, cyclohexyl or halogen; and R$_{30}$ and R$_{31}$ independently of one another are phenyl which is substituted in at least one of the two positions ortho to the titanium-carbon bond by fluorine atoms or CF$_3$ and which can contain as further substituents on the aromatic ring polyoxaalkyl or pyrrolinyl unsubstituted or substituted one or two times by C$_1$–C$_{12}$alkyl, di(C$_1$–C$_{12}$alkyl)aminomethyl, morpholinomethyl, C$_2$–C$_4$alkenyl, methoxymethyl, ethoxymethyl, trimethylsilyl, formyl, methoxy or phenyl, or R$_{30}$ and R$_{31}$ are

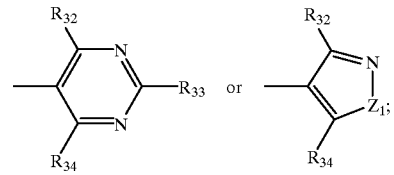

R$_{32}$, R$_{33}$ and R$_{34}$ independently of one another are hydrogen, halogen C$_2$–C$_{12}$alkenyl, C$_1$–C$_{12}$alkoxy, C$_2$–C$_{12}$alkoxy which is interrupted by one to four O atoms, cyclohexyloxy, cyclopentyloxy, phenoxy or benzyloxy, or are biphenylyl or phenyl unsubstituted or substituted by C$_1$–C$_4$alkoxy, halogen, phenylthio or C$_1$–C$_4$alkylthio, where R$_{32}$ and R$_{34}$ are not both simultaneously hydrogen and, in the radical

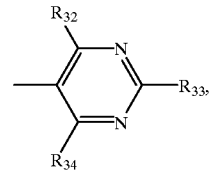

at least one radical R$_{32}$ or R$_{34}$ is C$_1$–C$_{12}$alkoxy, C$_2$–C$_{12}$alkoxy interrupted by one to four O atoms, or is cyclohexyloxy, cyclopentyloxy, phenoxy or benzyloxy;

Z$_1$ is O, S or NR$_{35}$; and

R$_{35}$ is C$_1$–C$_8$alkyl, phenyl or cyclohexyl.

R$_{17}$ as C$_1$–C$_{18}$alkyl can have the same definitions as described for R$_1$. In addition, R$_{19}$ and R$_{20}$ as C$_1$–C$_6$alkyl and R$_{18}$ as C$_1$–C$_4$alkyl can have the same definitions as described for R$_1$ up to the respective number of C atoms.

C$_1$–C$_{18}$alkyl can have the same definitions as described for R$_1$.

C$_1$–C$_{18}$alkoxy is, for example, branched or unbranched alkoxy such as methyloxy, ethyloxy, n-propyloxy, isopropyloxy, n-butyloxy, isobutyloxy, sec-butyloxy, tert-butyloxy, pentyloxy, hexyloxy, heptyloxy, octyloxy, 2,4,4-trimethylpent-1-yloxy, 2-ethylhexyloxy, nonyloxy, decyloxy, dodecyloxy or octadecyloxy.

$C_2$–$C_{12}$alkoxy has the definitions indicated above up to the corresponding number of C atoms.

$R_{19}$, $R_{20}$ and $R_{18}$ as $C_1$–$C_{16}$alkoxy can have the same definitions as described for $R_{17}$ up to the corresponding number of C atoms, and are preferably decyloxy, methoxy and ethoxy, especially methoxy and ethoxy.

The radical —O($CH_2CH_2O$)$_m$—$C_1$–$C_{16}$alkyl stands for 1 to 20 successive ethylene oxide units whose chain ends with a $C_1$–$C_{16}$alkyl. Preferably, m is from 1 to 10, for example from 1 to 8, in particular from 1 to 6. The chain of ethylene oxide units is preferably terminated by a $C_1$–$C_{10}$-, for example $C_1$–$C_8$-, in particular by a $C_1$–$C_4$alkyl.

$R_{23}$ as a substituted phenylthio ring is preferably p-tolylthio.

$R_{25}$ and $R_{26}$ as $C_1$–$C_{20}$alkyl are linear or branched and are, for example $C_1$–$C_{12}$-, $C_1$–$C_8$-, $C_1$–$C_6$- or $C_1$–$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl, octadecyl, nonadecyl or icosyl. $R_{25}$ as alkyl is preferably $C_1$–$C_8$alkyl.

$R_{25}$, $R_{26}$ and $R_{27}$ as substituted phenyl are substituted one to five times, for example once, twice or three times, especially three or two times, on the phenyl ring.

Substituted phenyl, naphthyl or biphenylyl is, for example, substituted by linear or branched $C_1$–$C_4$alkyl such as methyl, ethyl, n-propyl, i-propyl, n-butyl, i-butyl, s-butyl or t-butyl or by linear or branched $C_1$–$C_4$alkoxy such as methoxy, ethoxy, n-propoxy, i-propoxy, n-butoxy, i-butoxy, s-butoxy or t-butoxy, preferably by methyl or methoxy.

Where $R_{25}$, $R_{26}$ and $R_{27}$ are an S- or N-containing 5- or 6-membered heterocyclic ring then they are, for example, thienyl, pyrrolyl or pyridyl.

In the term di($C_1$–$C_{12}$alkyl)aminomethyl, $C_1$–$C_{12}$alkyl has the same definitions as indicated for $R_1$.

$C_2$–$C_{12}$alkenyl is linear or branched, can be mono- or polyunsaturated and is, for example, allyl, methallyl, 1,1-dimethylaliyl, 1-butenyl, 2-butenyl, 1,3-pentadienyl, 1-hexenyl or 1-octenyl, especially allyl.

$C_1$–$C_4$alkylthio is linear or branched and is, for example, methylthio, ethylthio, n-propylthio, i-propylthio, n-butylthio, i-butylthio, s-butylthio or t-butylthio, preferably methylthio.

$C_2$–$C_4$alkenyl is, for example, allyl, methallyl, 1-butenyl or 2-butenyl.

Halogen is fluorine, chlorine, bromine or iodine, preferably, fluorine, chlorine or bromine.

The term polyoxaalkyl embraces $C_2$–$C_{20}$alkyl interrupted by 1 to 9 O atoms and stands, for example, for structural units such as $CH_3$—O—$CH_2$—, $CH_3CH_2$—O—$CH_2CH_2$—, $CH_3O[CH_2CH_2O]_y$—, where y=1–9, —($CH_2CH_2O)_7CH_2CH_3$, —$CH_2$—$CH(CH_3)$—O—$CH_2$—$CH_2CH_3$.

Preference is given to compositions in which $R_{17}$ is hydrogen, —$OCH_2CH_2$—$OR_{21}$, morpholino, $SCH_3$, a group

or a group

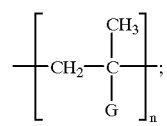

$R_{18}$ is hydroxyl, $C_1$–$C_{16}$alkoxy, morpholino or dimethylamino;

$R_{19}$ and $R_{20}$ independently of one another are, $C_1$–$C_4$alkyl, phenyl, benzyl or $C_1$–$C_{16}$alkoxy, or $R_{19}$ and $R_{20}$, together with the carbon atom to which they are attached, form a cyclohexyl ring;

$R_{21}$ is hydrogen or

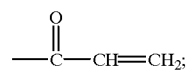

$R_{22}$, $R_{23}$ and $R_{24}$ are hydrogen;

$R_{25}$ is $C_1$–$C_{12}$alkyl, unsubstituted phenyl or phenyl substituted by $C_1$–$C_{12}$alkyl and/or $C_1$–$C_{12}$alkoxy;

$R_{26}$ is

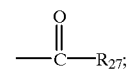

and $R_{27}$ is phenyl which is substituted by $C_1$–$C_4$alkyl and/or $C_1$–$C_4$alkoxy.

Preferred compounds of the formulae XII, XIII, XIV and XV are α-hydroxycyclohexyl phenyl ketone or 2-hydroxy-2-methyl-1-phenylpropanone, (4-methylthiobenzoyl)-1-methyl-1-morpholinoethane, (4-morpholino-benzoyl)-1-benzyl-1-dimethylamino-propane, benzil dimethyl ketal, (2,4,6-trimethylbenzoyl)phenylphosphine oxide, bis(2,6-dimethoxybenzoyl)(2,4,4-trimethylpent-1-yl)phosphine oxide, bis(2,4,6-trimethylbenzoyl)-phenylphosphine oxide or bis-(2,4,6-trimethylbenzoyl)(2,4-dipentoxyphenyl) phosphine oxide and dicyclopentadienylbis(2,6-difluoro-3-pyrrolo)titanium.

Preference is also given to compositions in which, in the formula XII, $R_{19}$ and $R_{20}$ independently of one another are $C_1$–$C_6$alkyl or, together with the carbon atom to which they are attached, form a cyclohexyl ring and $R_{18}$ is hydroxyl.

The proportion of compounds of the formula I (=photoinitiator component (b)) in the mixture with compounds of the formulae XII, XIII, XIV and/or XV (=photoinitiator component (c)) is from 5 to 99%, e.g. 20–80%, preferably from 25 to 75%.

Also important are compositions in which, in the compounds of the formula XII, $R_{19}$ and $R_{20}$ are identical and are methyl and $R_{18}$ is hydroxyl or i-propoxy.

Preference is likewise given to compositions comprising compounds of the formula I and compounds of the formula XIV in which $R_{25}$ is unsubstituted or mono- to tri-$C_1$–$C_{12}$alkyl- and/or -$C_1$–$C_{12}$alkoxy-substituted phenyl or $C_1$–$C_{12}$alkyl;

$R_{26}$ is the group

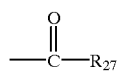

or phenyl; and $R_{27}$ is phenyl substituted one to three times by $C_1$–$C_4$alkyl or $C_1$–$C_4$alkoxy.

Of interest above all are compositions as described above which comprise photoinitiator mixtures of the formulae II, XII, XIII, XIV and/or XV and which are liquid at room temperature.

The preparation of compounds of the formulae XII, XIII, XIV and XV is generally known, and some of the compounds are obtainable commercially. The preparation of oligomeric compounds of the formula XII is described, for example, in EP-A-161 463. A description of the preparation of compounds of the formula XIII can be found, for example, in EP-A-209 831. The preparation of compounds of the formula XIV is disclosed, for example, in EP-A 7508, EP-A 184 095 and GB-A 2 259 704. The preparation of compounds of the formula XV is described, for example, in EP-A 318 894, EP-A 318 893 and EP-A 565 488.

The photopolymerizable compositions generally comprise 0.05 to 15% by weight, preferably 0.1 to 5% by weight, of the photoinitiator, based on the composition. The amount refers to the sum of all photoinitiators added, if mixtures of initiators are employed. Accordingly, the amount either refers to the photoinitiator (b) or the photoinitiators (b)+(c).

The photopolymerizable compositions can be used for various purposes, for example as printing ink, as a clear finish, as a white finish, for example for wood or metal, as powder coating, as a coating material, inter alia for paper, wood, metal or plastic, as a daylight-curable coating for the marking of buildings and roadmarking, for photographic reproduction techniques, for holographic recording materials, for image recording techniques or to produce printing plates which can be developed with organic solvents or with aqueous alkalis, for producing masks for screen printing, as dental filling compositions, as adhesives, as pressure-sensitive adhesives, as laminating resins, as etch resists or permanent resists, and as solder masks for electronic circuits, for producing three-dimensional articles by mass curing (UV curing in transparent moulds) or by the stereolithography technique, as is described, for example, in U.S. Pat. No. 4,575,330, to produce composite materials (for example styrenic polyesters, which may, if desired, contain glass fibres and/or other fibres and other auxiliaries) and other thick-layered compositions, for coating or sealing electronic components and chips, or as coatings for optical fibres. The compositions according to the invention are further suitable for the production of medical equipment, auxiliaries or implants.

Further the compositions according to the invention are suitable for the preparation of gels with thermotropic properties, as for example described in DE-A 19700064 and EP-A 678534.

The novel photoinitiator systems may additionally be employed as initiators for emulsion polymerizations, pearl polymerizations or suspension polymerizations, as polymerization initiators for fixing ordered states of liquid-crystalline monomers and oligomers, or as initiators for fixing dyes on organic materials.

In coating materials, use is frequently made of mixtures of a prepolymer with polyunsaturated monomers, which may additionally include a monounsaturated monomer as well. It is the prepolymer here which primarily dictates the properties of the coating film, and by varying it the skilled worker is able to influence the properties of the cured film. The polyunsaturated monomer functions as a crosslinking agent which renders the film insoluble. The monounsaturated monomer functions as a reactive diluent, which is used to reduce the viscosity without the need to employ a solvent.

Unsaturated polyester resins are usually used in two-component systems together with a monounsaturated monomer, preferably with styrene. For photoresists, specific one-component systems are often used, for example polymaleimides, polychalcones or polyimides, as described in DE-A 2308830.

The novel photoinitiator systems and mixtures thereof can also be used for the polymerization of radiation-curable powder coatings. The powder coatings can be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (for example methyl methylacrylamidoglycolate) and a novel free-radical photoinitiator, such formulations being as described, for example, in the paper "Radiation Curing of Powder Coating", Conference Proceedings, Radtech Europe 1993 by M. Wittig and Th. Gohmann. The powder coatings can also contain binders, as are described, for example, in DE-A 4228514 and in EP-A 636669. Free-radically UV-curable powder coatings can also be formulated by mixing unsaturated polyester resins with solid acrylates, methacrylates or vinyl ethers and with a novel photoinitiator (or photoinitiator mixture). The powder coatings may also comprise binders as are described, for example, in DE-A 4228514 and in EP-A 636669. The UV-curable powder coatings may additionally comprise white or coloured pigments. For example, preferably rutiletitanium dioxide can be employed in concentrations of up to 50% by weight in order to give a cured powder coating of good hiding power. The procedure normally comprises electrostatic or tribostatic spraying of the powder onto the substrate, for example metal or wood, melting of the powder by heating, and, after a smooth film has formed, radiation-curing of the coating with ultraviolet and/or visible light, using for example medium-pressure mercury lamps, metal halide lamps or xenon lamps. A particular advantage of the radiation-curable powder coatings over their heat-curable counterparts is that the flow time after melting the powder particles can be delayed in order to ensure the formation of a smooth, high-gloss coating. In contrast to heat-curable systems, radiation-curable powder coatings can be formulated to melt at lower temperatures without the unwanted effect of shortening their lifetime. For this reason, they are also suitable as coatings for heat-sensitive substrates, for example wood or plastics. In addition to the novel photoinitiator systems, the powder coating formulations may also include UV absorbers. Appropriate examples are listed above in sections 1–8.

The novel photocurable compositions are suitable, for example, as coating materials for substrates of all kinds, for example wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which it is intended to apply a protective layer or, by means of imagewise exposure, to generate an image.

Coating of the substrates can be carried out by applying to the substrate a liquid composition, a solution or a suspension. The choice of solvents and the concentration depend principally on the type of composition and on the coating technique. The solvent should be inert, i.e. it should not undergo a chemical reaction with the components and should be able to be removed again, after coating, in the course of drying. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

The solution is applied uniformly to a substrate by means of known coating techniques, for example by spin coating, dip coating, knife coating, curtain coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, by transferring the layer via lamination.

The quantity applied (coat thickness) and the nature of the substrate (layer support) are dependent on the desired field of application. The range of coat thicknesses generally comprises values from about 0.1 μm to more than 100 μm.

The novel radiation-sensitive compositions further find application as negative resists, having a very high sensitivity to light and being able to be developed in an aqueous alkaline medium without swelling. They are suitable as photoresists for electronics (electroplating resist, etch resist, solder resist), the production of printing plates, such as offset printing plates or screen printing plates, for the production of printing formes for relief printing, planographic printing, rotogravure or of screen printing formes, for the production of relief copies, for example for the production of texts in braille, for the production of stamps, for use in chemical milling or as a microresist in the production of integrated circuits. The possible layer supports, and the processing conditions of the coating substrates, are just as varied.

The compositions according to the invention also find application for the production of one- or more-layered materials for the image recording ore image reproduction (copies, reprography), which may be uni- or polychromatic. Furthermore the materials are suitable for colour proofing systems. In this technology formulations containing microcapsules can be applied and for the image production the radiation curing can be followed by a thermal treatment. Such systems and technologies and their applications are for example disclosed in U.S. Pat. No. 5,376,459.

Substrates used for photographic information recordings include, for example, films of polyester, cellulose acetate or polymer-coated papers; substrates for offset printing formes are specially treated aluminium, substrates for producing printed circuits are copper-clad laminates, and substrates for producing integrated circuits are silicon wafers. The layer thicknesses for photographic materials and offset printing formes is generally from about 0.5 μm to 10 μm, while for printed circuits it is from 1.0 μm to about 100 μm.

Following the coating of the substrates, the solvent is removed, generally by drying, to leave a coat of the photoresist on the substrate.

The term "imagewise" exposure includes both, exposure through a photomask comprising a predetermined pattern, for example a slide, as well as exposure by means of a laser or light beam, which for example is moved under computer control over the surface of the coated substrate and in this way produces an image, and irradiation with computer-controlled electron beams. It is also possible to use masks made of liquid crystals that can be adressed pixel by pixel to generate digital images, as is, for example, described by A. Bertsch, J. Y. Jezequel, J. C. Andre in Journal of Photochemistry and Photobiology A: Chemistry 1997, 107, p. 275–281 and by K.-P. Nicolay in Offset Printing 1997, 6, p. 34–37.

Following the imagewise exposure of the material and prior to development, it may be advantageous to carry out thermal treatment for a short time. In this case only the exposed sections are thermally cured. The temperatures employed are generally 50–150° C., preferably 80–130° C.; the period of thermal treatment is in general between 0.25 and 10 minutes.

The photocurable composition may additionally be used in a process for producing printing plates or photoresists as is described, for example, in DE-A 4013358. In such a process the composition is exposed for a short time to visible light with a wavelength of at least 400 nm, without a mask, prior to, simultaneously with or following imagewise irradiation. After the exposure and, if implemented, thermal treatment, the unexposed areas of the photosensitive coating are removed with a developer in a manner known per se.

As already mentioned, the novel compositions can be developed by aqueous alkalis. Particularly suitable aqueous-alkaline developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents.

Photocuring is of great importance for printings, since the drying time of the ink is a critical factor for the production rate of graphic products, and should be in the order of fractions of seconds. UV-curable inks are particularly important for screen printing and offset inks.

As already mentioned above, the novel mixtures are highly suitable also for producing printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent. Another field where photocuring is employed is the coating of metals, in the case, for example, of the coating of metal plates and tubes, cans or bottle caps, and the photocuring of polymer coatings, for example of floor or wall coverings based on PVC. Examples of the photocuring of paper coatings are the colourless varnishing of labels, record sleeves and book covers.

Also of interest is the use of the novel compounds and photoinitiator systems for curing shaped articles made from composite compositions. The composite compound consists of a self-supporting matrix material, for example a glass fibre fabric, or alternatively, for example, plant fibres [cf. K.-P. Mieck, T. Reussmann in Kunststoffe 85 (1995), 366–370], which is impregnated with the photocuring formulation. Shaped parts comprising composite compounds, when produced using the novel compounds, attain a high level of mechanical stability and resistance. The novel compounds can also be employed as photocuring agents in moulding, impregnating and coating compositions as are described, for example, in EP-A 7086. Examples of such compositions are gel coat resins, which are subject to stringent requirements regarding curing activity and yellowing resistance, and fibre-reinforced mouldings, for example, light diffusing panels which are planar or have lengthwise or crosswise corrugation. Techniques for producing such mouldings, such as hand lay-up, spray lay-up, centrifugal casting or filament winding, are described, for example, by P. H. Selden in "Glasfaserverstärkte Kunststoffe", page 610, Springer Verlag Berlin-Heidelberg-New York 1967. Examples of articles which can be produced by these techniques are boats, fibre board or chipboard panels with a double-sided coating of glass fibre-reinforced plastic, pipes, containers, etc. Further examples of moulding, impregnating and coating compositions are UP resin gel coats for mouldings containing glass fibres (GRP), such as corrugated sheets and paper laminates. Paper laminates may be based on urea resins or melamine resins. Prior to production of the laminate, the gel coat is produced on a support (for example a film). The novel photocurable compositions can also be used for casting resins or for embedding articles, for example electronic components, etc. Curing usually is carried out using medium-pressure mercury lamps as are conventional in UV curing. However, there is also particular interest in less intense lamps, for example of the type TL 40W/03 or TL40W/05. The intensity of these lamps corresponds approximately to that of sunlight. It is also possible to use direct sunlight for curing. A further advantage is that the composite composition can be removed from the light source in a partly cured, plastic state and can be shaped, with full curing taking place subsequently.

The compositions and compounds according to the invention can be used for the production of holographies, waveguides, optical switches wherein advantage is taken of the development of a difference in the index of refraction between irradiated and unirradiated areas.

The use of photocurable compositions for imaging techniques and for the optical production of information carriers is also important. In such applications, as already described above, the layer (wet or dry) applied to the support is irradiated imagewise, e.g through a photo-mask, with UV or visible light, and the unexposed areas of the layer are removed by treatment with a developer. Application of the photocurable layer to metal can also be carried out by electrodeposition. The exposed areas are polymeric through crosslinking and are therefore insoluble and remain on the support. Appropriate colouration produces visible images. Where the support is a metallized layer, the metal can, following exposure and development, be etched away at the unexposed areas or reinforced by electroplating. In this way it is possible to produce electronic circuits and photoresists.

The photosensitivity of the novel compositions can extend in general from about 200 nm to 600 nm (UV region). Suitable radiation is present, for example, in sunlight or light from artificial light sources. Consequently, a large number of very different types of light sources are employed. Both point sources and arrays ("lamp carpets") are suitable. Examples are carbon arc lamps, xenon arc lamps, medium-, high- and low-pressure mercury lamps, possibly with metal halide dopes (metal-halogen lamps), microwave-stimulated metal vapour lamps, excimer lamps, superactinic fluorescent tubes, fluorescent lamps, argon incandescent lamps, electronic flashlights, photographic flood lamps, light emitting diodes (LED), electron beams and X-rays. The distance between the lamp and the substrate to be exposed in accordance with the invention may vary depending on the intended application and the type and output of lamp, and may be, for example, from 2 cm to 150 cm. Laser light sources, for example excimer lasers, such as krypton F lasers for exposure at 248 nm are also suitable. Lasers in the visible region can also be employed. By this method it is possible to produce printed circuits in the electronics industry, lithographic offset printing plates or relief printing plates, and also photographic image recording materials.

Also provided for by the invention is the use of the above-described compositions for the preparation of pigmented and nonpigmented coating materials, printing inks, powder coatings, printing plates, adhesives, dental compositions, optical waveguides, optical switches, colourproofing systems, composite compositions, glass fibre cable coatings, screen-printing stencils, resist materials, the encapsulation of electrical and electronic components, the production of magnetic recording materials, the production of three-dimensional objects by means of stereolithography, for photographic reproductions, and as image-recording material, especially for holograms.

The invention therefore also provides a process for photopolymerizing non-volatile monomeric, oligomeric or polymeric compounds having at least one ethylenically unsaturated double bond, which comprises irradiating a composition as described above with light in the range from 200 to 600 nm.

Also in accordance with the invention is this process for preparing pigmented and nonpigmented coating materials, printing inks, powder coatings, printing plates, adhesives, dental compositions, optical waveguides, optical switches, colourproofing systems, composite compositions, glass fibre cable coatings, screen-printing stencils, resist materials, the encapsulation of electrical and electronic components, the production of magnetic recording materials, the production of three-dimensional objects by means of stereolithography, for photographic reproductions, and for the production of image-recording material, especially for holograms.

The invention likewise provides a coated substrate which is coated on at least one surface with a composition as described above, and a process for the photographic preparation of relief images in which a coated substrate is subjected to imagewise exposure and then the unexposed areas are removed with a solvent. Imagewise exposure can take place through a mask or by means of a laser beam. Of particular interest in this context is exposure, as already mentioned above, by means of a laser beam.

The compounds of the invention are compounds of low volatility with only a slight inherent odour, which are easy to incorporate into polymerizable formulations.

The examples which follow illustrate the invention. As in the remainder of the description and in the claims, parts and percentages are by weight unless stated otherwise.

EXAMPLE 1

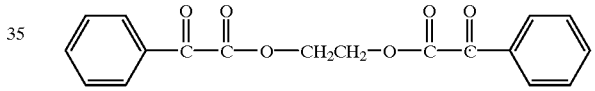

Under a stream of nitrogen, 188.90 g of methyl phenylglyoxylate are heated with stirring at 120° C. with 36 g of ethylene glycol and 10 g of dibutyltin oxide. The methanol formed is removed by distillation. After the end of the reaction, the reaction mixture is allowed to cool to 20° C. and is separated by means of flash chromatography, giving 81.40 g of the title compound having a melting point of 91–92° C.

| Elemental analysis: | C [%] | H [%] |
|---|---|---|
| calc.: | 66.26 | 4.32 |
| found: | 66.23 | 4.47 |

EXAMPLES 2–9

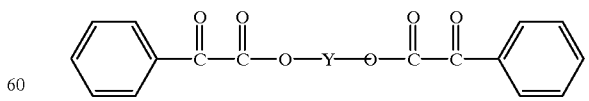

The compounds of Examples 2–9 are prepared by a method similar to that described in Example 1 using, rather than ethylene glycol, the particular corresponding diol (HO—Y—OH) as starting compound. The compounds and their physical data are set out in Table 1.

TABLE 1

| Example | Y | Melting point [° C.] | Elemental analysis calculated found | | |
|---|---|---|---|---|---|
| | | | C [%] | H [%] | S [%] |
| 2 | —CH$_2$CH$_2$—O—CH$_2$CH$_2$— | liquid | 64.86<br>64.90 | 4.90<br>4.91 | — |
| 3 | —CH$_2$CH$_2$—O—CH$_2$CH$_2$—O—CH$_2$CH$_2$— | liquid | 62.87<br>63.07 | 5.71<br>5.77 | — |
| 4 | —CH$_2$—(C$_6$H$_4$)—CH$_2$— | 90–91 | 71.64<br>71.15 | 4.51<br>4.63 | — |
| 5 | —(C$_6$H$_4$)— | 154–155 | 70.20<br>69.91 | 3.77<br>3.80 | — |
| 6 | —(CH$_2$)$_6$— | 57 | 69.10<br>69.05 | 5.80<br>5.83 | — |
| 7 | —CH(CH$_3$)CH$_2$— | <20 | 67.06<br>67.61 | 4.74<br>4.76 | — |
| 8 | —CH$_2$C(CH$_3$)$_2$CH$_2$— | <20 | 68.47<br>69.37 | 5.47<br>5.53 | — |
| 9 | —CH$_2$CH$_2$—S—CH$_2$CH$_2$— | liquid | 62.17<br>61.90 | 4.70<br>4.70 | 8.30<br>8.29 |

EXAMPLES 10–12

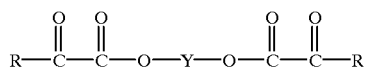

The compounds of Examples 10–12 are prepared by a method similar to that described in Example 1 using, rather than ethylene glycol, the particular corresponding diol (HO—Y—OH) as starting compound and, rather than the methyl phenylglyoxalate, the respective compound substituted appropriately on the aromatic structure. The structures of the compounds and their physical data are reproduced in Table 2.

TABLE 2

| Example | Y | R | Elemental analysis calculated found | | |
|---|---|---|---|---|---|
| | | | C [%] | H [%] | S [%] |
| 10 | —CH$_2$CH$_2$— | —C$_6$H$_4$—OCH$_3$ | 62.17<br>61.78 | 4.71<br>4.74 | — |
| 11 | —(CH$_2$)$_2$—O—(CH$_2$)$_2$— | —C$_6$H$_4$—SCH$_3$ | 57.12<br>56.64 | 4.80<br>4.86 | 13.86<br>13.37 |
| 12 | —(CH$_2$)$_2$—O—(CH$_2$)$_2$— | —C$_6$H$_3$(SC$_4$H$_9$)(SC$_4$H$_9$) | 59.75<br>59.86 | 6.99<br>7.15 | 17.72<br>17.64 |

EXAMPLE 13

Curing an Epoxy Acrylate Clearcoat

An epoxy acrylate clearcoat is prepared from 89 parts of Ebecryl® 604 (epoxy acrylate resin, UCB, Belgium)

10 parts of Sartomer® SR 344 (polyethylene glycol-400 diacrylate)

1 part of Ebecryl® 350 (silicone diacrylate, UCB, Belgium)

The particular photoinitiator to be tested is dissolved in the formulation in the concentration indicated in Table 3. Using a 6 μm slotted doctor blade, the photocurable formulation is applied to sheets of cardboard and is exposed to light on a conveyor belt which is passed below two 80 W/cm medium-pressure mercury lamps (AETEK device, Plainfield, Ill.). The test ascertains the highest possible belt speed at which a wipefast cured surface is formed. The higher this belt speed the more reactive the photoinitiator tested. In a second test series, the formulation is applied to light-coloured chipboard panels using a 100 μm slotted doctor blade and is cured at a belt speed of 10 m/min (exposure takes place with two 80 W/cm medium-pressure mercury lamps; AETEK device, Plainfield, Ill.). The König pendulum hardness (DIN 53157) of the cured coat is measured. The higher the pendulum hardness value the more effective the photoinitiator used. The results are listed in Table 3.

TABLE 3

| Photoinitiator from Example | Concentration [%] | Wipefastness [m/min] | Pendulum hardness [s] |
| --- | --- | --- | --- |
| 1 | 2 | 40 | 167 |
| 1 | 3 | 50 | 171 |
| 2 | 2 | 35 | 168 |
| 2 | 3 | 50 | 165 |

EXAMPLE 14
Curing a Urethane Acrylate Clearcoat

The following formulation is prepared:

72.6% oligomer AJ 18 (polyurethane acrylate from SNPE, France)

17.1% N-vinylpyrrolidone 10.3% butanediol diacrylate

The photoinitiators to be tested are incorporated into the above-described mixture in a concentration of 2%. Using a 200 μm slotted doctor blade, coats are applied to light-coloured flexible PVC (floor covering) and are exposed to light on a conveyor belt which is passed below two 80 W/cm medium-pressure mercury lamps (AETEK device, Plainfield, Ill.). The test ascertains the highest possible belt speed at which a wipefast cured surface is formed. The higher this belt speed the more reactive the photoinitiator tested. The results are set out in Table 4.

TABLE 4

| Photoinitiator from Example | Wipefasteness [m/min] |
| --- | --- |
| 1 | 20 |
| 2 | 20 |

EXAMPLE 15
Curing an Aqueous Formulation

The photoinitiators to be tested are incorporated at room temperature in a concentration of 1% (based on the formulation with water component) into Laromer® PE55W (aqueous polyester acrylate emulsion, BASF, Germany). Using a 15 μm slotted doctor blade, the formulation is applied to sheets of cardboard and is dried at about 150° C. for 5 minutes using a hot-air fan. Curing takes place by exposure under two 80 W/cm medium-pressure mercury lamps by passing the sample, on a conveyor belt, under the lamps (AETEK device, Plainfield, Ill.). The test ascertains the highest possible belt speed at which a wipefast cured surface is formed. The higher this belt speed the more reactive the photoinitiator tested. In a second test series, coats of the formulation are applied to light-coloured chipboard panels using a 100 μm slotted doctor blade, the resulting coats are dried in a convection oven at 80° C. for 3 minutes and exposed to light as described above at a belt speed of 3 m/min. Subsequently, the Konig pendulum hardness (DIN 53157) is measured. The higher the pendulum hardness value the more effective the photoinitiator used. The results are given in Table 5.

TABLE 5

| Photoinitiator from Example | Wipefastness [m/min] | Pendulum hardness [s] |
| --- | --- | --- |
| 1 | 10 | 144 |
| 2 | 10 | 144 |

EXAMPLE 16
Curing a White Polyester Acrylate Paint

A solid mixture is prepared from 75 parts by weight of the photoinitiator of Example 1 and 25 parts by weight of bis(2,4,6-trimethylbenzoyl)phenylphosphine oxide. 3% of this photoinitiator mixture is incorporated into a white paint formulation comprising the following components 67.5 parts of Ebecryl® 830 (polyester acrylate resin, UCB, Belgium)

5.0 parts of hexanediol diacrylate 2.5 parts of trimethylolpropane triacrylate 25.0 parts of titanium dioxide, rutile type (RTC-2 from Tioxide, France)

A 100 μm slotted doctor blade is used to apply a coat of the photocurable formulation to a chipboard panel, and this coat is exposed with an 80 W/cm medium-pressure mercury lamp (Canrad-Hanovia, USA) at a belt speed of 3 m/min. A wipefast and fully cured coat of paint is obtained whose Konig pendulum hardness (DIN 53157) is 120 s.

EXAMPLE 17
Curing an Epoxy Acrylate Clearcoat

The photoinitiator of Example 10 is incorporated in a concentration of 2% into a formulation as described in Example 13 and is tested as described in Example 13. The formulation is wipefast at a belt speed of 50 m/min and the pendulum hardness is 192 s.

EXAMPLE 18
Curing an Aqueous System

The photoinitiators of Examples 10 and 11 are incorporated in a concentration of 2% by weight, based on the resin concent of the formulation, into a 50% aqueous polyester acrylate emulsion (Laromer PE 55W from BASF). Using a 15 μm spiral doctor blade, coats are applied to sheets of cardboard, are dried at 150° C. for 5 minutes using a hot-air fan and then are exposed with two 80 W/cm medium-pressure mercury lamps in an AETEK processor (Plainfield, Ill.) at a belt speed of 10 m/min. Thoroughly cured, glossy coating films are obtained with both of the initiators used.

What is claimed is:

1. A compound of the formula I

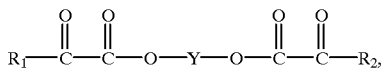

(I)

in which

R$_1$ and R$_2$ independently of one another are a group of the formula II

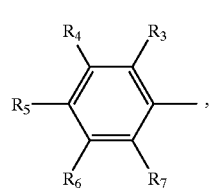

(II)

or a naphthyl, anthracyl, phenanthryl, furyl, thienyl, pyrrolyl, oxinyl, dioxinyl, or pyridyl radical, the naphthyl, anthracyl, phenanthryl, furyl, thienyl, pyrrolyl, oxinyl, dioxinyl, and pyridyl radicals being unsubstituted or substituted by C$_1$–C$_8$alkyl, phenyl, OR$_8$, SR$_9$ and/or NR$_{10}$R$_{11}$, and where the substituents OR$_8$, SR$_9$, NR$_{10}$R$_{11}$ can form 5- or 6-membered rings by way of the radicals R$_8$, R$_9$, R$_{10}$ and/or R$_{11}$ with further substituents on the naphthyl, anthracyl, phenanthryl, furyl, thienyl, pyrrolyl, oxinyl, dioxinyl, or pyridyl ring or with one of the C atoms of the naphthyl, anthracyl, phenanthryl, furyl, thienyl, pyrrolyl, oxinyl, dioxinyl, or pyridyl ring;

R$_3$, R$_4$, R$_5$, R$_6$ and R$_7$ independently of one another are hydrogen or are C$_1$–C$_{12}$alkyl which is unsubstituted or substituted by OH, C$_1$–C$_4$alkoxy, phenyl, naphthyl, halogen, CN or —OCOR$_{12}$, or a mixture thereof, or are C$_2$–C$_{12}$alkyl which is interrupted by one or more O atoms, or R$_3$, R$_4$, R$_5$, R$_6$ and R$_7$ are OR$_8$, SR$_9$, NR$_{10}$R$_{11}$, halogen or phenyl which is unsubstituted or substituted by one or two C$_1$–C$_4$alkyl and/or one or two C$_1$–C$_4$alkoxy substituents, where the substituents OR$_8$, SR$_9$, NR$_{10}$R$_{11}$ can form 5- or 6-membered rings by way of the radicals R$_8$, R$_9$, R$_{10}$ and/or R$_{11}$ with further substituents on the phenyl ring or with one of the C atoms of the phenyl ring;

R$_8$ and R$_9$ independently of one another are hydrogen or are C$_1$–C$_{12}$alkyl which is unsubstituted or substituted by OH, C$_1$–C$_4$alkoxy, phenyl, phenoxy and/or OCOR$_{12}$, or a mixture thereof, or are C$_2$–C$_{12}$alkyl which is interrupted by one or more O atoms, or R$_8$ and R$_9$ are unsubstituted or C$_1$–C$_4$alkoxy-, phenyl- and/or C$_1$–C$_4$alkyl-substituted phenyl, C$_3$–C$_6$alkenyl, cyclopentyl, cyclohexyl or naphthyl;

R$_{10}$ and R$_{11}$, independently of one another are hydrogen or are C$_1$–C$_{12}$alkyl which is unsubstituted or substituted by OH, C$_1$–C$_4$alkoxy or phenyl or a mixture thereof, or are C$_2$–C$_{12}$alkyl which is interrupted by one or more O atoms, or R$_{10}$ and R$_{11}$ are phenyl, —COR$_{12}$ or SO$_2$R$_{13}$, or R$_{10}$ and R$_{11}$, together with the nitrogen atom to which they are attached, form a 5-, 6- or 7-membered ring which may additionally be interrupted by —O— or —NR$_{14}$—;

R$_{12}$ is C$_1$–C$_8$alkyl or is phenyl which is unsubstituted or substituted by one to three C$_1$–C$_4$alkyl and/or one to three C$_1$–C$_4$alkoxy substituents;

R$_{13}$ is C$_1$–C$_{12}$alkyl, phenyl or 4-methylphenyl;

R$_{14}$ is hydrogen or is C$_1$–C$_8$alkyl which is unsubstituted or substituted by OH or C$_1$–C$_4$alkoxy or is phenyl which is unsubstituted or substituted by OH, C$_1$–C$_4$alkyl or C$_1$–C$_4$alkoxy;

Y is C$_1$–C$_{12}$alkylene, C$_4$–C$_8$-alkenylene, C$_4$–C$_8$alkynylene, cyclohexylene, C$_4$–C$_{40}$alkylene interrupted one or more times by —O—, —S— or —NR$_{15}$—, or is phenylene, or Y is a group of the formula III, IV, V, VI, VII, VIII, IX, X or XI

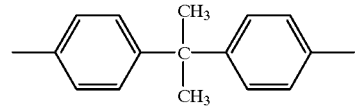

(III)

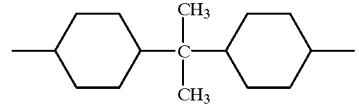

(IV)

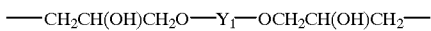

(V)

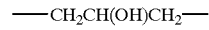

(VI)

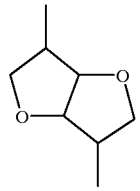

(VII)

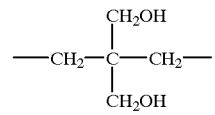

(VIII)

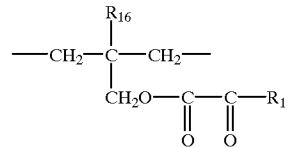

(IX)

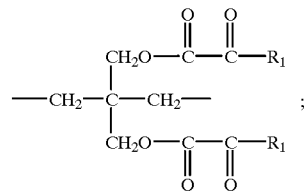

(X)

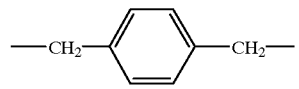

(XI)

Y$_1$ is as defined for Y with the exception of the formula V;

R$_{15}$ is hydrogen, C$_1$–C$_{12}$alkyl or phenyl; and

R$_{16}$ is hydrogen, CH$_2$OH or C$_1$–C$_4$alkyl.

2. A compound according to claim 1, in which $R_1$ and $R_2$ are a radical of the formula II.

3. A compound according to claim 1, in which $R_1$ and $R_2$ are identical.

4. A compound according to claim 1, in which Y is phenylene, $C_2$–$C_8$alkylene, $C_4$alkenylene, $C_4$alkynylene or cyclohexylene, or is $C_4$–$C_{18}$alkylene interrupted one or more times by —O—, or Y is a group of the formula V, VI, IX, X or XI.

5. A compound according to claim 1, in which $R_3$, $R_4$, $R_5$, $R_6$ and $R_7$ independently of one another are hydrogen, $C_1$–$C_4$alkyl, chlorine, $OR_8$, $SR_9$ or $NR_{10}R_{11}$ and where the substituent $OR_8$ can form 5- or 6-membered rings by way of the radical $R_8$ with further substituents on the phenyl ring or with one of the C atoms of the phenyl ring.

6. A compound according to claim 1, in which $R_1$ and $R_2$ are a radical of the formula II, $R_4$ and $R_5$ independently of one another are hydrogen, $OR_8$ or $SR_9$, $R_3$, $R_6$ and $R_7$ are hydrogen, $R_8$ and $R_9$ are $C_1$–$C_4$alkyl and Y is linear or branched $C_2$–$C_6$alkylene, phenylene or a group of the formula XI or is $C_4$–$C_6$alkylene interrupted once or twice by —O— or —S—.

7. A photopolymerizable composition comprising
(a) at least one ethylenically unsaturated photopolymerizable compound,
(b) as photoinitiator, at least one compound of the formula I according to claim 1.

8. A composition according to claim 7, comprising in addition to component (b) further photoinitiators (c) and/or additives (d).

9. A composition according to claim 8, in which the additional photoinitiators (c) are compounds of the formula XII, XIII, XIV or mixtures thereof,

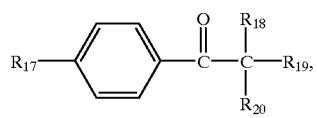
(XII)

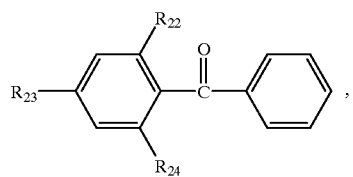
(XIII)

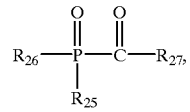
(XIV)

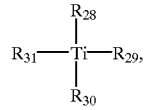
(XV)

in which
$R_{17}$ is hydrogen, $C_1$–$C_{18}$alkyl, $C_1$–$C_{18}$alkoxy, —OCH$_2$CH$_2$—OR$_{21}$, morpholino, SCH$_3$, a group

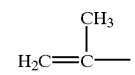

or a group

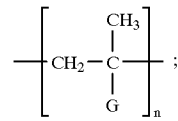

n has a value from 2 to 10;
G is the radical

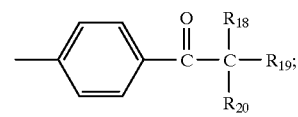

$R_{18}$ is hydroxyl, $C_1$–$C_{16}$alkoxy, morpholino, dimethylamino or —O(CH$_2$CH$_2$O)$_m$—C$_1$–C$_{16}$alkyl;

$R_{19}$ and $R_{20}$ independently of one another are hydrogen, $C_1$–$C_6$alkyl, phenyl, benzyl, $C_1$–$C_{16}$alkoxy or —O(CH$_2$CH$_2$O)$_m$—C$_1$–C$_{16}$alkyl, or $R_{19}$ and $R_{20}$, together with the carbon atom to which they are attached, form a cyclohexyl ring;

m is a number 1–20;

where $R_{18}$, $R_{19}$ and $R_{20}$ are not all simultaneously $C_1$–$C_{16}$alkoxy or —O(CH$_2$CH$_2$O)$_m$—C$_1$–C$_{16}$alkyl, and $R_{21}$ is hydrogen,

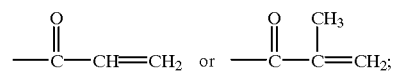

$R_{22}$ and $R_{24}$ independently of one another are hydrogen or methyl;

$R_{23}$ is hydrogen, methyl or phenylthio, where the phenyl ring of the phenylthio radical can be substituted in positions 4, 2, 2,4 or 2,4,6 by $C_1$–$C_4$alkyl;

$R_{25}$ and $R_{26}$ independently of one another are $C_1$–$C_{20}$alkyl, cyclohexyl, cyclopentyl, phenyl, naphthyl or biphenylyl, where the radicals cyclohexyl, cyclopentyl, phenyl, naphthyl or biphenylyl are unsubstituted or subsituted by halogen, $C_1$–$C_{12}$alkyl and/or $C_1$–$C_{12}$alkoxy, or $R_{25}$ is an S- or N-containing 5-or 6-membered heterocyclic ring, or are

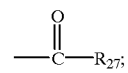

$R_{27}$ is cyclohexyl, cyclopentyl, phenyl, naphthyl or biphenylyl, where the radicals cyclohexyl, cyclopentyl, phenyl, naphthyl or biphenylyl are unsubstituted or substituted by halogen, $C_1$–$C_4$alkyl and/or $C_1$–$C_4$alkoxy, or $R_{27}$ is an S- or N-containing 5- or 6-membered heterocyclic ring;

$R_{28}$ and $R_{29}$ independently of one another are cyclopentadienyl which is unsubstituted or substituted once, twice or three times by $C_1$–$C_{18}$alkyl, $C_1$–$C_{18}$alkoxy, cyclopentyl, cyclohexyl or halogen; and $R_{30}$ and $R_{31}$ independently of one another are phenyl which is substituted in at least one of the two positions ortho to the titanium-carbon bond by fluorine atoms or $CF_3$ and which can contain as further substituents on the aromatic ring polyoxaalkyl or pyrrolinyl unsubstituted or substituted one or two times by $C_1$–$C_{12}$alkyl, di($C_1$–$C_{12}$alkyl)aminomethyl, morpholinomethyl, $C_2$–$C_4$alkenyl, methoxymethyl, ethoxymethyl, trimethylsilyl, formyl, methoxy or phenyl, or $R_{30}$ and $R_{31}$ are

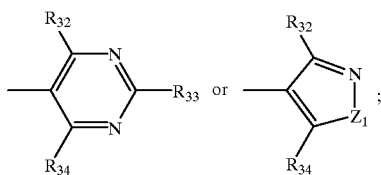

$R_{32}$, $R_{33}$ and $R_{34}$ independently of one another are hydrogen, halogen $C_2$–$C_{12}$alkenyl, $C_1$–$C_{12}$alkoxy, $C_2$–$C_{12}$alkoxy which is interrupted by one to four O atoms, cyclohexyloxy, cyclopentyloxy, phenoxy or benzyloxy, or are biphenylyl or phenyl unsubstituted or substituted by $C_1$–$C_4$alkoxy, halogen, phenylthio or $C_1$–$C_4$alkylthio, where $R_{32}$ and $R_{34}$ are not both simultaneously hydrogen and, in the radical

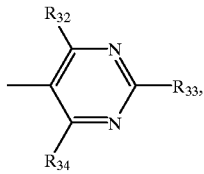

at least one radical $R_{32}$ or $R_{34}$ is $C_1$–$C_{12}$alkoxy, $C_2$–$C_{12}$alkoxy interrupted by one to four O atoms, or is cyclohexyloxy, cyclopentyloxy, phenoxy or benzyloxy;

$Z_1$ is O, S or $NR_{35}$; and $R_{35}$ is $C_1$–$C_8$alkyl, phenyl or cyclohexyl.

10. A composition according to claim 9, in which $R_{17}$ is hydrogen, —$OCH_2CH_2$—$OR_{21}$, morpholino, $SCH_3$, a group

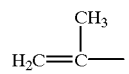

or a group

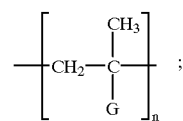

$R_{18}$ is hydroxyl, $C_1$–$C_{16}$alkoxy, morpholino or dimethylamino;

$R_{19}$ and $R_{20}$ independently of one another are, $C_1$–$C_4$alkyl, phenyl, benzyl or $C_1$–$C_{16}$alkoxy, or $R_{19}$ and $R_{20}$, together with the carbon atom to which they are attached, form a cyclohexyl ring;

$R_{21}$ is hydrogen or

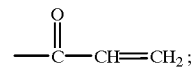

$R_{22}$, $R_{23}$ and $R_{24}$ are hydrogen;

$R_{25}$ is $C_1$–$C_{12}$alkyl, unsubstituted phenyl or phenyl substituted by $C_1$–$C_{12}$alkyl and/or $C_1$–$C_{12}$alkoxy;

$R_{26}$ is

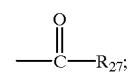

and $R_{27}$ is phenyl which is substituted by $C_1$–$C_4$alkyl and/or $C_1$–$C_4$alkoxy.

11. A composition according to claim 7, containing 0.05–15% by weight of the photoinitiator component (b) and/or 0.05–15% by weight of the photoinitiator components (b)+(c).

12. A process for photopolymerizing non-volatile monomeric, oligomeric or polymeric compounds having at least one ethylenically unsaturated double bond, which comprises irradiating a composition according to claim 7 with light in the range from 200 to 600 nm.

13. A process according to claim 12 for preparing pigmented and nonpigmented coating materials, printing inks, powder coatings, printing plates, adhesives, dental compositions, optical waveguides, optical switches, colour-proofing systems, composite compositions, glass fibre cable coatings, screen-printing stencils, resist materials, the encapsulation of electrical and electronic components, the production of magnetic recording materials, the production of three-dimensional objects by means of stereolithography, for photographic reproductions, and for the production of image-recording material.

14. A coated substrate which is coated on at least one surface with a composition according to claim 7.

15. A process for the photographic preparation of relief images in which a coated substrate according to claim 14 is subjected to imagewise exposure and then the unexposed areas are removed with a solvent, it being possible for the imagewise exposure to take place either through a mask or by means of a laser beam.

* * * * *